United States Patent
Al-Dahle et al.

(10) Patent No.: US 8,988,471 B2
(45) Date of Patent: Mar. 24, 2015

(54) SYSTEMS AND METHODS FOR DYNAMIC DWELLING TIME FOR TUNING DISPLAY TO REDUCE OR ELIMINATE MURA ARTIFACT

(75) Inventors: Ahmad Al-Dahle, Santa Clara, CA (US); David A. Stronks, San Jose, CA (US); Hopil Bae, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 185 days.

(21) Appl. No.: 13/601,801

(22) Filed: Aug. 31, 2012

(65) Prior Publication Data

US 2013/0329057 A1 Dec. 12, 2013

Related U.S. Application Data

(60) Provisional application No. 61/657,652, filed on Jun. 8, 2012.

(51) Int. Cl.
*G09G 5/10* (2006.01)

(52) U.S. Cl.
USPC .............................. 345/690; 345/87; 345/89

(58) Field of Classification Search
USPC ............... 345/690, 87, 89, 102, 207, 204, 77; 324/760.01; 349/192
See application file for complete search history.

(56) References Cited

U.S. PATENT DOCUMENTS

| | | | | |
|---|---|---|---|---|
| 5,764,209 A * | 6/1998 | Hawthorne et al. | ............. | 345/87 |
| 6,067,061 A * | 5/2000 | Friedman | .................... | 345/74.1 |
| 6,559,826 B1 * | 5/2003 | Mendelson et al. | .......... | 345/102 |
| 6,747,619 B1 * | 6/2004 | Tanahashi et al. | ............. | 345/87 |
| 6,853,387 B2 * | 2/2005 | Evanicky et al. | ............. | 345/690 |
| 2003/0072496 A1 * | 4/2003 | Woodell et al. | ............... | 382/260 |
| 2003/0214586 A1 * | 11/2003 | Lee et al. | ...................... | 348/180 |
| 2004/0070565 A1 * | 4/2004 | Nayar et al. | .................. | 345/156 |
| 2005/0277815 A1 * | 12/2005 | Taniguchi et al. | ............ | 600/300 |
| 2006/0061248 A1 * | 3/2006 | Cok et al. | ...................... | 313/110 |
| 2006/0238460 A1 * | 10/2006 | Huang | ............................. | 345/76 |
| 2007/0109245 A1 * | 5/2007 | Hwang | ........................... | 345/98 |
| 2007/0242064 A1 * | 10/2007 | Kuo | .............................. | 345/207 |
| 2008/0179595 A1 * | 7/2008 | Song et al. | ..................... | 257/59 |
| 2008/0180377 A1 * | 7/2008 | Meng | ............................. | 345/94 |
| 2009/0096729 A1 * | 4/2009 | Ozawa et al. | .................. | 345/87 |

* cited by examiner

*Primary Examiner* — Koosha Sharifi-Tafreshi

(74) *Attorney, Agent, or Firm* — Fletcher Yoder PC

(57) ABSTRACT

Systems and methods for calibrating an electronic display to reduce or eliminate a mura artifact are provided. The mura artifact may be due to differential behavior of common voltage layers (VCOMs) in the electronic display. One method for reducing or eliminating the mura artifact may involve turning on an electronic display and programming pixels the electronic display to a uniform gray level. An initial luminance value may be determined and, after waiting a period of time, a subsequent luminance of the pixels may be measured. When a difference between the subsequent luminance and initial luminance is within a threshold, the mura artifact may be understood to have settled and the electronic display may be calibrated.

22 Claims, 21 Drawing Sheets

SYSTEMS AND METHODS FOR DYNAMIC DWELLING TIME FOR TUNING DISPLAY TO REDUCE OR ELIMINATE MURA ARTIFACT

CROSS-REFERENCE TO RELATED APPLICATIONS

This application is a Non-Provisional Patent Application of U.S. Provisional Patent Application No. 61/657,652, entitled "Systems and Methods for Dynamic Dwelling Time for Tuning Display to Reduce or Eliminate Mura Artifact", filed Jun. 8, 2012, which are herein incorporated by reference.

In addition, the following patent applications, all filed on Jun. 8, 2012, are related: "Systems and Methods for Reducing or Eliminating Mura Artifact Using Contrast-Enhanced Imagery," U.S. Provisional Application Ser. No. 61/657,704; "Systems and Methods for Reducing or Eliminating Mura Artifact Using Image Feedback," U.S. Application Ser. No. 61/657,656; "Systems and Methods for Dynamic Dwelling Time For Tuning Display to Reduce or Eliminate Mura Artifact," U.S. Application Ser. No. 61/657,652; and "Systems and Methods for Mura Calibration Preparation," U.S. Application Ser. No. 61/657,701. The above applications are incorporated herein by reference in their entirety.

BACKGROUND

The present disclosure relates generally to electronic displays and, more particularly, to electronic displays tuned to reduce or eliminate mura artifacts.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Electronic displays commonly appear in electronic devices such as televisions, computers, and phones. One type of electronic display, known as a liquid crystal display (LCD), displays images by modulating the amount of light allowed to pass through a liquid crystal layer within pixels of the LCD. In general, LCDs modulate the light passing through each pixel by varying a voltage difference between a pixel electrode and a common electrode. This creates an electric field that causes the liquid crystal layer to change alignment. The change in alignment of the liquid crystal layer causes more or less light to pass through the pixel. By changing the voltage difference (often referred to as a data signal) supplied to each pixel, images are produced on the LCD.

Conventionally, the common electrodes of the pixels of the LCD are all formed from a single common voltage layer (VCOM). Thus, to the extent that undesirable bias voltages or voltage perturbations may occur in the VCOM, any resulting negative effects would be distributed over the entire LCD. When an LCD includes multiple VCOMs, however, it is believed that undesirable bias voltages or voltage perturbations may occur differentially on the various VCOMs. These differential bias voltages or voltage perturbations could produce visible artifacts known as muras, or largely permanent display screen artifacts.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of the present disclosure relate to systems, methods, and devices for reducing or eliminating mura artifacts in electronic displays, such as liquid crystal displays (LCDs) or organic light emitting diode (OLED) displays. In a particular example, it is believed that certain artifacts or muras could arise in an LCD having multiple distinct common voltage layers (VCOMs). For example, an LCD with VCOMs generally arranged in alternating rows and columns may exhibit a vertical stripe feature of merit. The vertical stripe feature of merit may appear as alternating light and dark vertical stripes along the LCD.

Various embodiments of the present disclosure may reduce or eliminate artifacts, including those due to differential voltages or voltage perturbations on multiple distinct VCOMs. In one example, an LCD having multiple VCOMs may be tuned automatically or by a human operator to reduce or eliminate mura artifacts. To do so, a display panel first may be programmed to display a uniform gray level in which artifacts are likely to be visible (e.g., gray level G63 of an 8-bit range from G0 to G255). A camera may obtain images of the display. The images may be amplified around the average luminance emitted by the display panel, thereby sharply increasing the contrast of the display panel artifacts occurring at that gray level. A human operator or an electronic control system may adjust certain display panel operating parameters until the artifacts are no longer visible. Such operating parameters may include, for example, a gate clock overlap, a gate clock fall time, a source output parking voltage, and/or a differential VCOM resistance.

In other examples, the display panel may be tuned at two or more gray levels. First, operating parameters that substantially eliminate mura artifacts at a first gray level (e.g., G63) may be determined. Next, the level of mura artifacts at a second gray level (e.g., G127) may be analyzed to determine whether the display panel is within a specification. Additionally or alternatively, other operating parameters may be determined that substantially eliminate mura artifacts at the second gray level (e.g., G127). Based on these operating parameters and the operating parameters that substantially eliminate mura artifacts at the first gray level (e.g., G63), intermediate operating parameters that allow the display panel to operate within a specified range may be determined.

Furthermore, the above methods may account for a variable transient effect of some mura artifacts and/or electrostatic discharge (ESD) on the display. For example, a display panel having multiple distinct VCOMs may be tuned, to prevent mura artifacts as well as other artifacts such as display flicker, after a VCOM transient dwelling time has elapsed. Certain embodiments of the present disclosure involve periodically testing a newly manufactured LCD until a mura artifact due to multiple distinct VCOMs has been reduced by a threshold amount. In addition, the display may be baked to reduce stray charges on the display before calibration. The resulting LCDs may be much less likely to exhibit artifacts due to the multiple distinct VCOMs.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
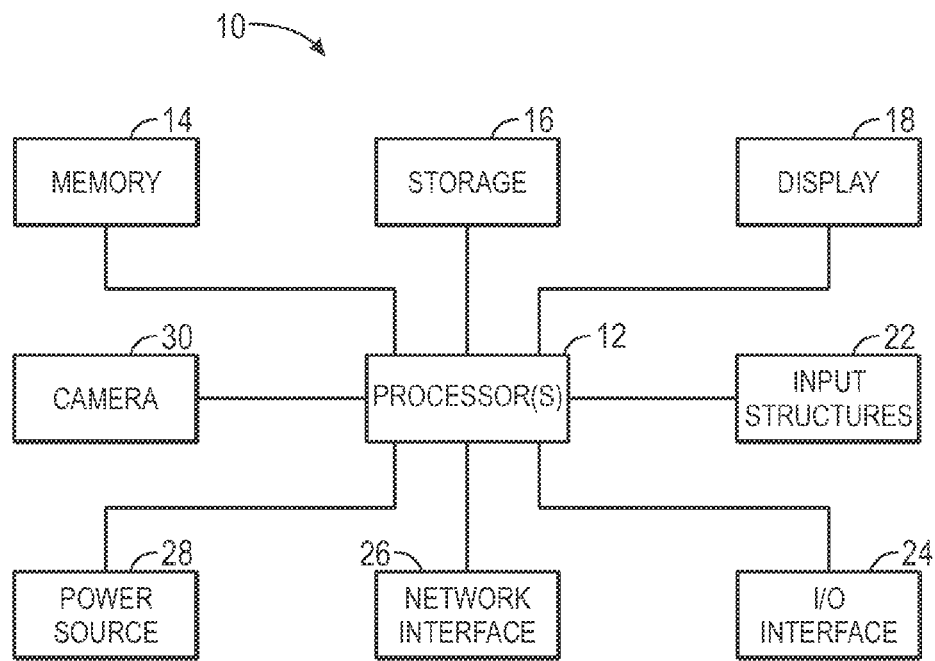
FIG. 1 is a block diagram of an electronic device with a liquid crystal display (LCD) tuned such that mura artifacts are reduced or eliminated, in accordance with an embodiment.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but may nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As mentioned above, it is believed that differential voltages and voltage perturbations on distinct common voltage layers (VCOMs) of a liquid crystal display (LCD) can produce artifacts known as muras. As used herein, the term "mura" refers to an artifact that is essentially permanent—that is, an artifact that can remain at least partially visible any time the display is on. The nature of the muras may depend on the arrangement of the internal components of the display. For instance, when the VCOMs are generally arranged in rows and columns, the resulting mura artifact may be known as a vertical stripe feature of merit (VSFOM). A VSFOM may manifest as light and dark stripes oriented parallel to source lines of the LCD.

Unsightly mura artifacts may be reduced or eliminated with proper tuning The embodiments of this disclosure relate to calibrating an LCD, or an electronic device including an LCD, such that artifacts or muras due to differential voltages on multiple distinct VCOMs are reduced or eliminated. In one example, a human operator or control system or an automatic control system may vary certain operating parameters of the LCD while viewing a contrast-enhanced image of the display. Varying the operating parameters—such as gate clock overlap, gate clock fall time, source output parking voltage, and/or differential resistance of various VCOMs—may vary the behavior of the mura artifact. Additionally or alternatively, the operating parameters may be adjusted according in a particular manner depending on the output of the display at different gray levels.

Before continuing, it should be appreciated that these techniques may be used in other contexts than just to reduce or eliminate VSFOM artifacts. Indeed, it is believed that any muras that can be varied by tuning various operating parameters, including but not limited to those operating parameters discussed in greater detail below, may be reduced or eliminated according to these techniques. Thus, although this disclosure uses the example of mura artifacts due to multiple distinct common voltage layers (VCOMs), the techniques of this disclosure should also be understood to be applicable to reduce or eliminate muras due to other causes.

Figure 2:
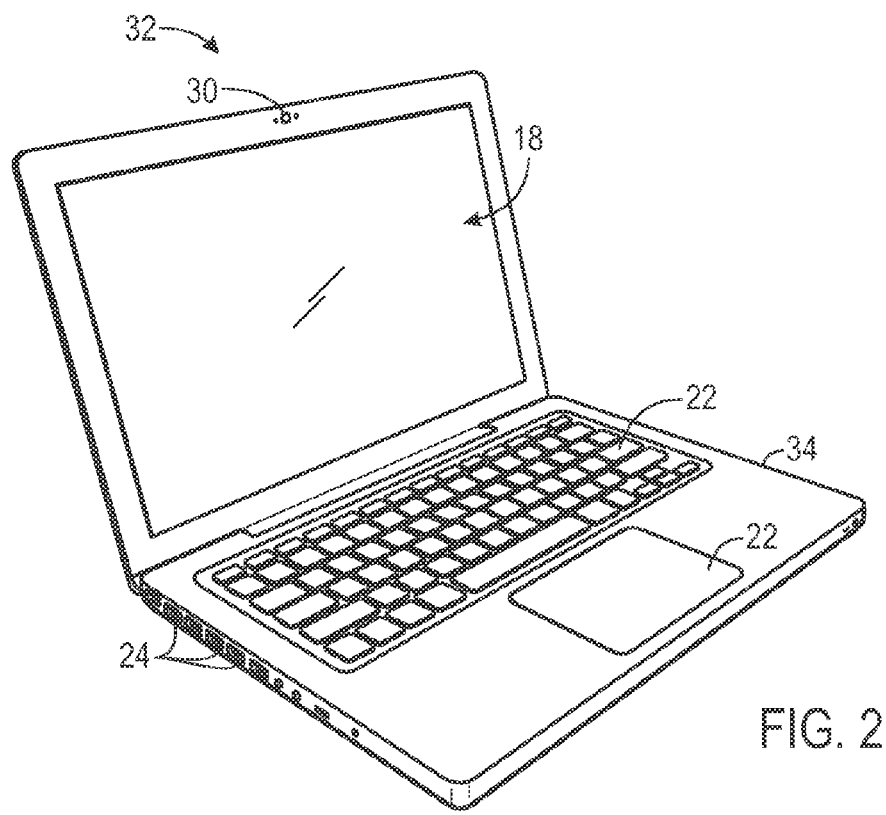
FIG. 2 is a perspective view of a notebook computer representing an embodiment of the electronic device of FIG. 1.
Figure 3:
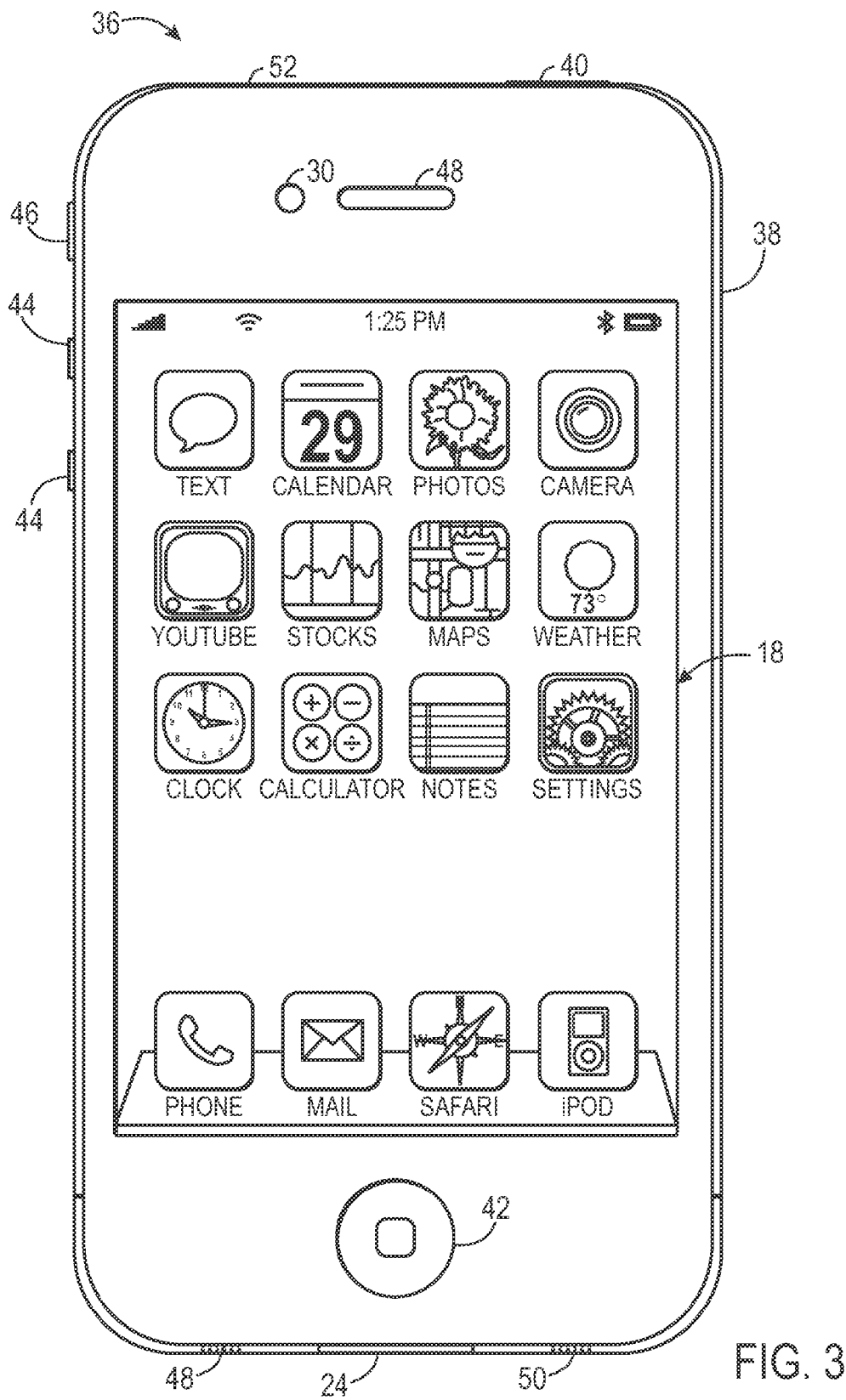
FIG. 3 is a front view of a handheld device representing another embodiment of the electronic device of FIG. 1.

With the foregoing in mind, many suitable electronic devices may employ electronic displays tuned such that mura artifacts are reduced or eliminated. For example, FIG. 1 is a block diagram depicting various components that may be present in an electronic device suitable for use with such a display. FIGS. 2 and 3 respectively illustrate perspective and front views of a suitable electronic device, which may be, as illustrated, a notebook computer or a handheld electronic device.

Turning first to FIG. 1, an electronic device 10 according to an embodiment of the present disclosure may include, among other things, one or more processor(s) 12, memory 14, nonvolatile storage 16, a display 18, input structures 22, an input/output (I/O) interface 24, network interfaces 26, a power source 28, and/or a camera 30. The various functional blocks shown in FIG. 1 may include hardware elements (including circuitry), software elements (including computer code stored on a computer-readable medium) or a combination of both hardware and software elements. It should be noted that FIG. 1 is merely one example of a particular implementation and is intended to illustrate the types of components that may be present in the electronic device 10. As will be appreciated, when there is a variation in voltage perturbation between VCOMs of the display 18, image quality of the display 18 may be distorted. For example, portions of the display 18 using one VCOM could produce different colors than portions of the display 18 using a different VCOM unless made more uniform, as taught by this disclosure.

By way of example, the electronic device 10 may represent a block diagram of the notebook computer depicted in FIG. 2, the handheld device depicted in FIG. 3, or similar devices. It should be noted that the processor(s) 12 and/or other data processing circuitry may be generally referred to herein as "data processing circuitry." This data processing circuitry may be embodied wholly or in part as software, firmware, hardware, or any combination thereof. Furthermore, the data processing circuitry may be a single contained processing module or may be incorporated wholly or partially within any of the other elements within the electronic device 10. As presented herein, the data processing circuitry may control the application of the added resistance as well as tuning of the resistance level to reduce a variation in voltage perturbation between two VCOMs (e.g., a column VCOM and a row VCOM) of the display 18.

In the electronic device 10 of FIG. 1, the processor(s) 12 and/or other data processing circuitry may be operably coupled with the memory 14 and the nonvolatile memory 16 to execute instructions. Such programs or instructions executed by the processor(s) 12 may be stored in any suitable article of manufacture that includes one or more tangible, computer-readable media at least collectively storing the instructions or routines, such as the memory 14 and the nonvolatile storage 16. The memory 14 and the nonvolatile storage 16 may include any suitable articles of manufacture for storing data and executable instructions, such as random-access memory, read-only memory, rewritable flash memory, hard drives, and optical discs. Also, programs (e.g., an operating system) encoded on such a computer program product may also include instructions that may be executed by the processor(s) 12.

The display 18 may be a touch-screen liquid crystal display (LCD), for example, which may enable users to interact with a user interface of the electronic device 10. In some embodiments, the electronic display 18 may be a MultiTouch™ display that can detect multiple touches at once. As will be described further below, the display 18 may include at least to distinct common voltage layers (VCOMs). An additional resistance may be added to at least one of these VCOMs to cause that VCOM to respond to voltage perturbations in a similar way as other VCOMs. By reducing variations in voltage perturbations on the VCOMs, color reproduction on the display 18 may be more uniform. As provided in an example discussed below, the electronic device 10 may include circuitry to control the resistance(s) of at least one of the VCOMs of the display 18.

The input structures 22 of the electronic device 10 may enable a user to interact with the electronic device 10 (e.g., pressing a button to increase or decrease a volume level). The I/O interface 24 may enable electronic device 10 to interface with various other electronic devices, as may the network interfaces 26. The network interfaces 26 may include, for example, interfaces for a personal area network (PAN), such as a Bluetooth network, for a local area network (LAN), such as an 802.11x Wi-Fi network, and/or for a wide area network (WAN), such as a 3G or 4G cellular network. The power source 28 of the electronic device 10 may be any suitable source of power, such as a rechargeable lithium polymer (Li-poly) battery and/or an alternating current (AC) power converter. The camera(s) 30 may capture images. The electronic device 10 may, in some embodiments, use images of the display 18 (e.g., as reflected by a mirror) to calibrate the display 18.

The electronic device 10 may take the form of a computer or other type of electronic device. Such computers may include computers that are generally portable (such as laptop, notebook, and tablet computers) as well as computers that are generally used in one place (such as conventional desktop computers, workstations and/or servers). In certain embodiments, the electronic device 10 in the form of a computer may be a model of a MacBook®, MacBook® Pro, MacBook Air®, iMac®, Mac® mini, or Mac Pro® available from Apple Inc. By way of example, the electronic device 10, taking the form of a notebook computer 32, is illustrated in FIG. 2 in accordance with one embodiment of the present disclosure. The depicted computer 32 may include a housing 34, a display 18, input structures 22, and ports of an I/O interface 24. In one embodiment, the input structures 22 (such as a keyboard and/or touchpad) may be used to interact with the computer 32, such as to start, control, or operate a GUI or applications running on computer 32. A camera 30 may obtain video or still images. The display 18 may be tuned to reduce or eliminate mura artifacts.

FIG. 3 depicts a front view of a handheld device 36, which represents one embodiment of the electronic device 10. The handheld device 36 may represent, for example, a portable phone, a media player, a personal data organizer, a handheld game platform, or any combination of such devices. By way of example, the handheld device 36 may be a model of an iPod® or iPhone® available from Apple Inc. of Cupertino, Calif. In other embodiments, the handheld device 36 may be a tablet-sized embodiment of the electronic device 10, which may be, for example, a model of an iPad® available from Apple Inc.

The handheld device 36 may include an enclosure 38 to protect interior components from physical damage and to shield them from electromagnetic interference. The enclosure 38 may surround the display 18. The I/O interfaces 24 may open through the enclosure 38 and may include, for example, a proprietary I/O port from Apple Inc. to connect to external devices.

User input structures 40, 42, 44, and 46, in combination with the display 18, may allow a user to control the handheld device 36. For example, the input structure 40 may activate or deactivate the handheld device 36, the input structure 42 may navigate a user interface to a home screen, a user-configurable application screen, and/or activate a voice-recognition feature of the handheld device 36, the input structures 44 may provide volume control, and the input structure 46 may toggle between vibrate and ring modes. A microphone 48 may obtain a user's voice for various voice-related features, and a speaker 50 may enable audio playback and/or certain phone capabilities. A headphone input 52 may provide a connection to external speakers and/or headphones. A front-facing camera 30 may capture still images or video. The display 18 may be tuned to reduce or eliminate mura artifacts.

Figure 4:
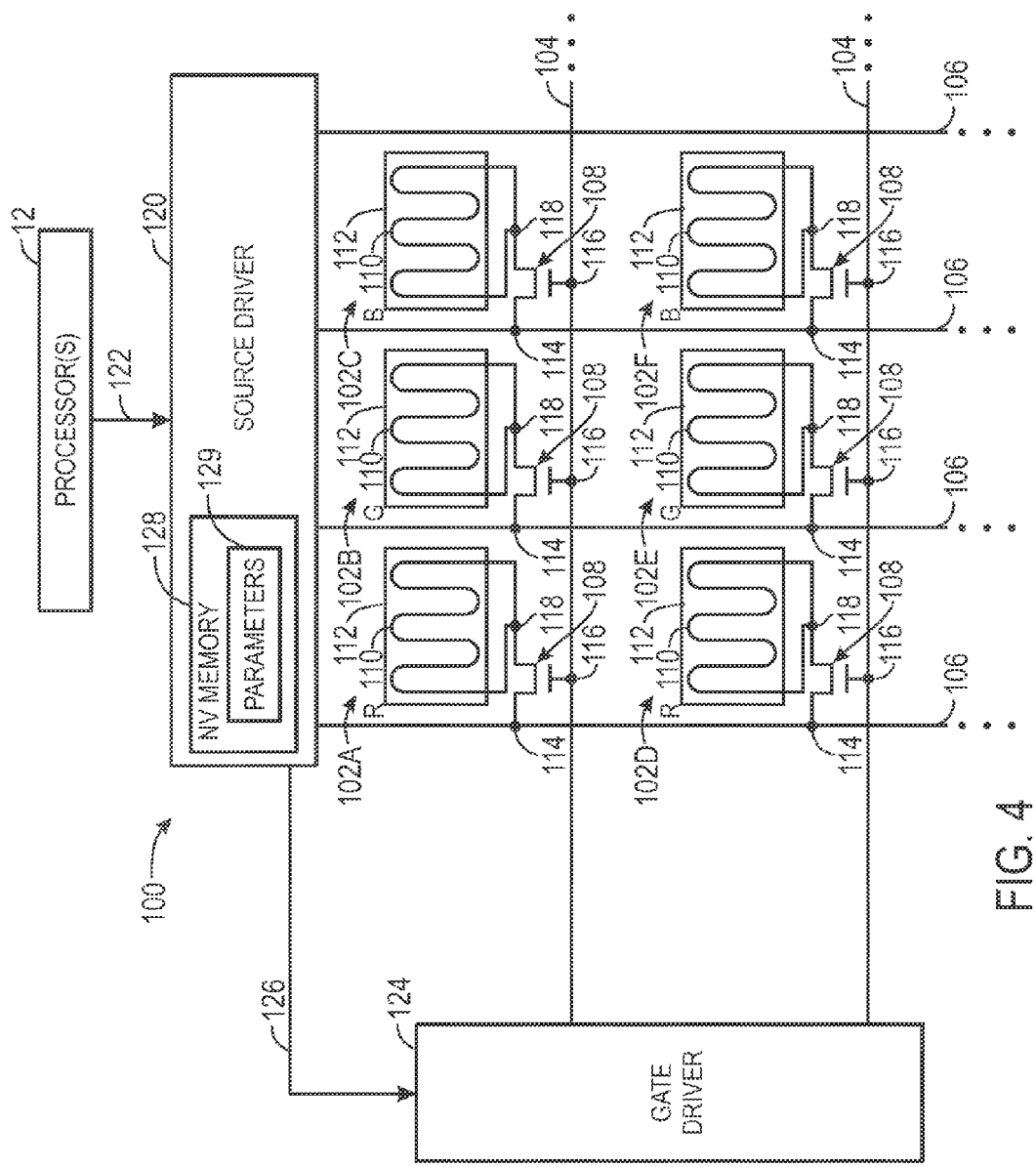
FIG. 4 is a circuit diagram illustrating display circuitry of the LCD, in accordance with an embodiment.

The display 18 may operate by activating and programming a number of picture elements, or pixels. These pixels may be generally arranged in a pixel array 100, as shown in FIG. 4. The pixel array 100 of the display 18 may include a number of unit pixels 102 disposed in a pixel array or matrix. In such an array, each unit pixel 102 may be defined by an intersection of gate lines 104 (also referred to as scanning lines) and source lines 106 (also referred to as data lines). Although only six unit pixels 102 are shown (102A-102F), it should be understood that in an actual implementation, the pixel array 100 may include hundreds or thousands of such unit pixels 102. Each of the unit pixels 102 may represent one of three subpixels that respectively filter only one color (e.g., red, blue, or green) of light. For purposes of the present disclosure, the terms "pixel," "subpixel," and "unit pixel" may be used largely interchangeably.

In the example of FIG. 4, each unit pixel 102 includes a thin film transistor (TFT) 108 for switching a data signal supplied to a respective pixel electrode 110. The potential stored on the pixel electrode 110 relative to a potential of a common electrode 112 may generate an electrical field sufficient to alter the arrangement of a liquid crystal layer of the display 18. When the arrangement of the liquid crystal layer changes, the amount of light passing through the pixel 102 also changes. A source 114 of each TFT 108 may connect to a source line 106 and a gate 116 of each TFT 108 may connect to a gate line 104. A drain 118 of each TFT 108 may be connect to a respective pixel electrode 110. Each TFT 108 may serve as a switching element that may be activated and deactivated by a scanning or activation signal on the gate lines 104.

When activated, a TFT 108 may pass the data signal from its source line 106 onto its pixel electrode 110. As noted above, the data signal stored by the pixel electrode 110 may be used to generate an electrical field between the respective pixel electrode 110 and a common electrode 112. This electrical field may align the liquid crystal molecules within the liquid crystal layer to modulate light transmission through the pixel 102. Thus, as the electrical field changes, the amount of light passing through the pixel 102 may increase or decrease. In general, light may pass through the unit pixel 102 at an intensity corresponding to the applied voltage from the source line 106.

These signals and other operating parameters of the display 18 may be controlled by integrated circuits (ICs) 121 of the display 18. These driver ICs 121 of the display 18 may include a processor, microcontroller, or application specific integrated circuit (ASIC). The driver ICs 121 may be chip-on-glass (COG) components on a TFT glass substrate, components of a display flexible printed circuit (FPC), and/or components of a printed circuit board (PCB) that is connected to the TFT glass substrate via the display FPC. Further, the driver ICs 121 of the display 18 may include the source driver 120 may include any suitable article of manufacture having one or more tangible, computer-readable media for storing instructions that may be executed by the driver ICs 121.

For instance, a source driver integrated circuit (IC) 120 may receive image data 122 from the processor(s) 12 and send corresponding image signals to the unit pixels 102 of the pixel array 100. The source driver 120 may also couple to a gate driver integrated circuit (IC) 124 that may activate or deactivate rows of unit pixels 102 via the gate lines 104. As such, the source driver 120 may provide timing signals 126 to the gate driver 124 to facilitate the activation/deactivation of individual rows (i.e., lines) of pixels 102. In other embodiments, timing information may be provided to the gate driver 124 in some other manner.

The storage 16 of the electronic device 10 or local nonvolatile memory 128 of the display 18 may store values of certain operational parameters 129 of the display 18. The display driver ICs 121 may apply these operational parameters 129 of the display 18 to reduce or eliminate mura artifacts on the display 18. As will be discussed below, the operational parameters 129 may be programmed according to any suitable methods, including those discussed further below. Operational parameters 129 that may be programmed in the storage 16 and/or nonvolatile memory 128 may include a gate clock overlap, a gate clock fall time, a source output parking voltage, and/or a resistance of various common voltage layers (VCOMs) of the display 18.

Some mura artifacts may be due to the arrangement of common voltage layers (VCOMs) serving as common electrodes 112. In particular, when the VCOMs of the display 18 appear as rows and columns, striping muras known as vertical stripe features of merit (VSFOMs) may occur. One example arrangement of various VCOMs of the display 18 appears in FIG. 5. This arrangement could cause mura artifacts on the display 18 unless the operational parameters 129 are properly tuned.

Figure 5:
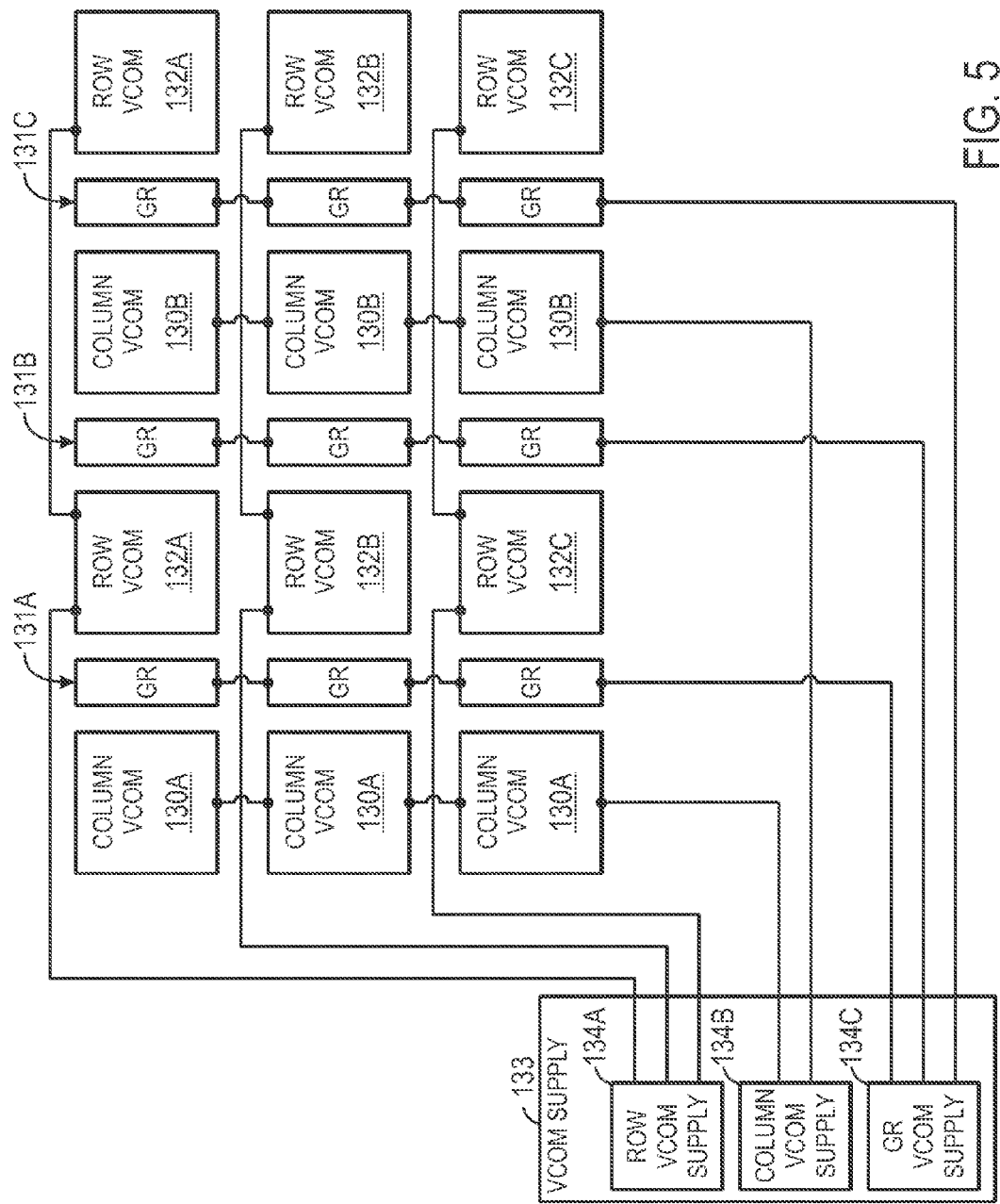
FIG. 5 is a schematic block diagram of the multiple VCOMs of the LCD, in accordance with an embodiment.

As seen in FIG. 5, the common voltage layers (VCOMs) that make up the common electrodes 112 may include column VCOMs 130, guard rail VCOMs 131, and row VCOMs 132. Although FIG. 5 shows only two column VCOMs 130A and 130B, three guard rail VCOMs 131, and two row VCOMs 132, an actual implementation of the display may include any suitable number of these components. A VCOM power supply 133 may supply power to the various VCOMs individually. Thus, a row VCOM supply 134A may supply power to the row VCOMs 132, a column VCOM supply may supply power to the column VCOMs 130, and a guard rail VCOM supply may supply power to the guard rail VCOMs 131.

Supplying power to the various VCOMs separately may allow the column VCOMs 130, guard rail VCOMs 131, and row VCOMs 132 to gather touch sense information when operating in a touch mode of operation. Specifically, though the column VCOMs 130, guard rail VCOMs 131, and row VCOMs 132 may be supplied the same direct current (DC) bias voltage, different alternating current (AC) voltages may be supplied and/or received on them at different times. Namely, the display 18 may be configured to switch between two modes of operation: a display mode and a touch mode. In the display mode, the row and column VCOMs 130, 132 operate in the aforementioned manner, in which an electric field is generated between the column and row VCOMs 130 and 132 and respective pixel electrodes 110. The electric field modulates the liquid crystal layer to let a certain amount of light pass through the pixel. Thus, an image may be displayed on the display 18 in the display mode. In the touch mode, the row VCOM 132 and the column VCOM 130 may be configured to sense a touch on the display 18. In certain embodiments, a stimulus signal or voltage may be provided by the row VCOM 132. The column VCOM 130 may be configured to receive a touch signal and output the data to be processed by the processor(s) 12. The touch signal may be generated when an operator touches the display 18 and capacitively couples with a portion of the row VCOM 132 and a portion of the column VCOM 130. Thus, the portion of the column VCOM 130 may receive a signal indicative of a touch.

Since the various VCOMs are electrically separated, it is possible for one to become biased more or less than another. This may produce mura artifacts on pixels along the rows and/or columns. When the display 18 operates according to certain operating parameters 129, however, mura artifacts may be substantially reduced or eliminated.

Operating Parameters

Any suitable operating parameters 129 may be adjusted to reduce or eliminate mura artifacts on the display 18. Among other things, the operating parameters 129 may include a gate clock overlap, a gate clock fall time, a source output parking voltage, and/or a differential resistance on the various VCOMs 130, 131, and/or 132. The adjustment of these various operating parameters 129 will be discussed further below.

Gate Clock Overlap and Gate Clock Fall Time

Adjusting gate clock overlap and gate clock fall time may reduce or eliminate muras. As will be discussed below, a gate clock overlap and a gate clock fall time may be programmed into the nonvolatile storage 128. Although the following examples of FIGS. 6 and 7 include circuitry that can automatically adjust the gate clock overlap and/or gate clock fall time, this circuitry may or may not be present in a display 18 that is calibrated according to the techniques of this disclosure. Accordingly, the examples of FIGS. 6 and 7 should be viewed in this light. Indeed, the principles of varying the gate clock overlap and gate clock fall time generally described in relation to FIGS. 6-9 below may be employed even when the gate clock overlap and gate clock fall time are adjusted manually or only when the display 18 is initially calibrated, as discussed further below.

Figure 6:
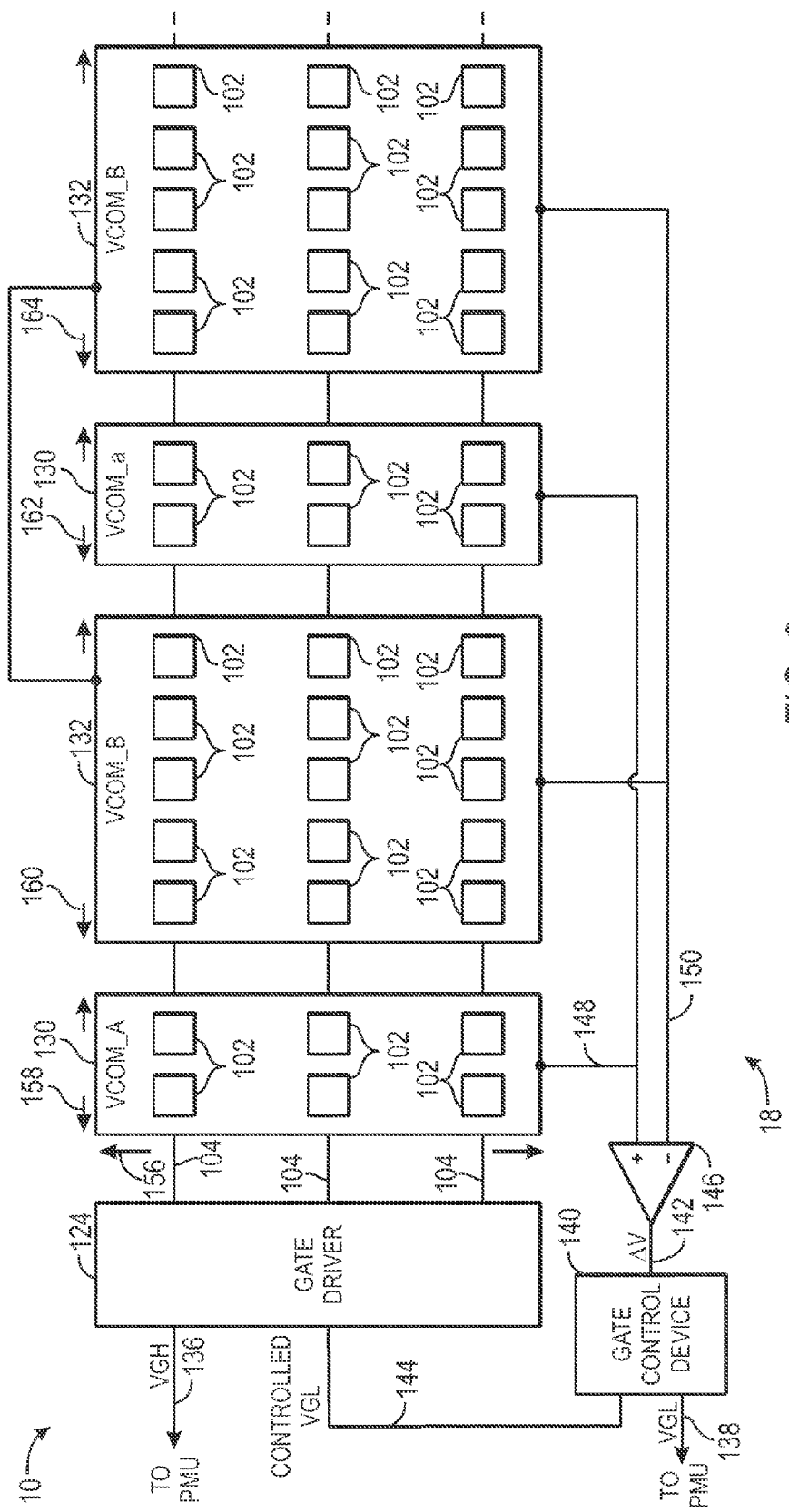
FIGS. 6 and 7 are block diagrams illustrating circuitry for controlling a gate clock overlap and/or gate clock fall time to improve image quality of the LCD, in accordance with an embodiment.

Embodiments involving adjustment of gate clock overlap and/or gate clock fall time relate to FIGS. 6-9. The adjustment of gate clock overlap and/or gate clock fall time may also be described in U.S. patent application Ser. No. 13/479,066, "DEVICES AND METHODS FOR REDUCING A VOLTAGE DIFFERENCE BETWEEN VCOMS OF A DISPLAY," which was filed on May 23, 2012, is assigned to Apple, Inc., and is incorporated by reference herein in its entirety. As seen in FIG. 6, the electronic device 10 may include a power management unit (PMU) 134. The PMU 134 is used to manage the power of the electronic device 10 and may control when power is applied to, or removed from, other components of the electronic device 10. For example, the PMU 134 provides a high gate voltage (VGH) 136 to the gate driver 124. In the present embodiment, the PMU 134 provides a low gate voltage (VGL) 138 to a gate control device 140. The gate control device 140 receives a voltage difference 142 and uses the voltage difference 142 to produce a controlled VGL 144 that is provided to the gate driver 124. As will be appreciated, the gate driver 124 may use the VGH 134 to apply an activation voltage to the gate lines 104, while the gate driver 124 may use the controlled VGL 144 to apply a deactivation voltage to the gate lines 104. As such, the gate driver 124 may be configured to couple together either the VGH 134 or the controlled VGL 144 to the gate lines 104.

A voltage sensing device 146 may be used to determine the voltage difference 142 between a first input 148 and a second input 150. In the present embodiment, the first input 148 is electrically coupled to the VCOM_A 130 and the second input 150 is electrically coupled to the VCOM_B 132. Accordingly, the voltage sensing device 146 detects the voltage difference 142 between the VCOM_A 130 and the VCOM_B 132. The voltage sensing device 146 may be any suitable voltage sensing device, such as an electronic amplifier (e.g., operational amplifier, differential amplifier, etc.).

As illustrated, the VCOM_A 130 and the VCOM_B 132 may not physically be the same size. Accordingly, the voltage difference 142 between the VCOM_A 130 and the VCOM_B 132 may result from resistive differences between the VCOM_A 130 and the VCOM_B 132. For example, when one of the gate lines 104 is deactivated, voltages stored on pixels 102 may change due to kickback voltage. As will be appreciated, the kickback voltage may not be the same for the VCOM_A 130 and the VCOM_B 132 due to their resistive differences. Therefore, the voltage sensing device 146 may detect the voltage difference 142.

To reduce the voltage difference 142, and therefore to reduce the visibility of the mura artifact, the voltage sensing device 146 provides the voltage difference 142 to the gate control device 140. The gate control device 140 may use the voltage difference 142 to modify the VGL 138 and provide the controlled VGL 144 to the gate driver 124. Specifically, after the gate control device 140 receives the VGL 138 indicating that the gates 116 should be deactivated, the gate control device 140 may modify the VGL 138 based at least partially on the voltage difference 142 to produce the controlled VGL 144. For example, the gate control device 140 may modify the rate that the activation voltage on the gate lines 104 transitions to the deactivation voltage. By modifying the rate that the gate lines 104 transition from the activation voltage to the deactivation voltage, the voltage difference 142 between the VCOM_A 130 and the VCOM_B 132 may be reduced. As will be appreciated, the gate control device 140 may use a mapping table to determine a rate that the gate lines 104 should transition to the deactivation voltage for a particular voltage difference 142. For example, the mapping table may include multiple voltage differences and rates of deactivation that correspond to each voltage difference.

The display 18 may have any number of VCOMs and the VCOMs may vary in size. FIG. 6 generally represents a diagram of circuitry of the electronic device 10 for controlling a voltage difference between sets of VCOMs of the display 18 to improve image quality of the display 18. Specifically, in the present embodiment, the display 18 includes the VCOM_A 130, the VCOM_B 132, a VCOM_C 152, and a VCOM_D 154. As illustrated, each of the VCOM_A 130, the VCOM_B 132, the VCOM_C 152, and the VCOM_D 154 generally have a length 156. Further, the VCOM_A 130 has a width 158, the VCOM_B 132 has a width 160, the VCOM_C 152 has a width 162, and the VCOM_D 154 has a width 164. In certain embodiments, the width 158 and the width 162 may generally be the same. In addition, the width 160 and the width 164 may generally be the same. Accordingly, the input 148 may be coupled to the VCOM_A 130 and the VCOM_C 152 (e.g., because they are generally the same size and will generally have similar resistive qualities), while the input 150 may be coupled to the VCOM_B 132 and the VCOM_D 154 (because they are generally the same size and will generally have similar resistive qualities). Therefore, in the present embodiment a single voltage sensing device may be used.

Figure 7:
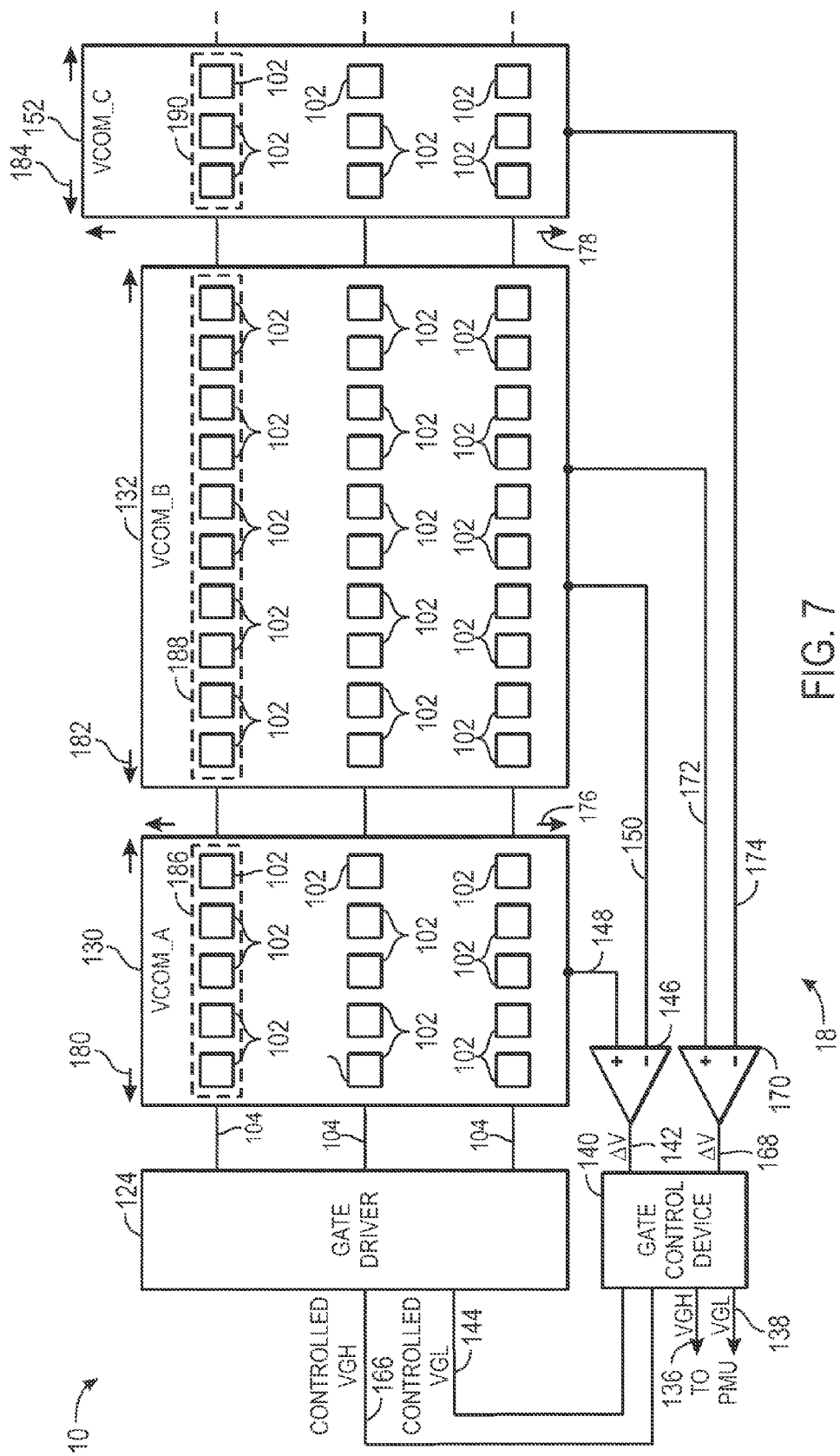

The display 18 may have more than one voltage sensing device (e.g., when there are more than two sizes of VCOMs). Accordingly, FIG. 7 illustrates one embodiment of circuitry of the electronic device 10 having multiple voltage sensing devices for sensing voltage differences between VCOMs of the display 18. In the present embodiment, the gate control device 140 is configured to receive the VGH 136 and the VGL 138. As such, the gate control device 140 provides a controlled VGH 166 and the controlled VGL 144 to the gate driver 124. Thus, the gate control device 140 may control the rates and/or timing of the activation and deactivation voltages that are applied to the gates 116 via the gate lines 104, as explained in detail below in relation to FIG. 9.

Further, the gate control device 140 receives a second voltage difference 168 from a second voltage sensing device 170. As illustrated, the voltage sensing device 146 receives inputs 148 and 150, which are electrically coupled to the VCOM_A 130 and the VCOM_B 132, respectively. The second voltage sensing device 170 receives inputs 172 and 174, which are electrically coupled to the VCOM_B 132 and the VCOM_C 152, respectively. Accordingly, the gate control device 140 may receive the voltage difference 142 (e.g., the voltage difference between the VCOM_A 130 and the VCOM_B 132) and the voltage difference 170 (e.g., the voltage difference between the VCOM_B 132 and the VCOM_C 152). Although the gate control device 140 does not receive a voltage difference between the VCOM_A 130 and the VCOM_C 152, the gate control device 140 may determine such a voltage difference. The gate control device 140 may use a mapping table where each row includes two voltage differences (e.g., for two voltage sensing devices) that together correspond to a rate of deactivation for the two voltage differences.

As illustrated, the VCOM_A 130 and the VCOM_B 132 may each have a length 176, while the VCOM_C 152 has a length 178. Further, the VCOM_A 130, the VCOM_B 132, and the VCOM_C 152 may have widths 180, 182, and 184, respectively. Accordingly, the VCOM_A 130, the VCOM_B 132, and the VCOM_C 152 may each be a different size and therefore may have different resistive characteristics. As such, two voltage sensing devices 146 and 170 may be used to detect the voltage differences between the VCOMs. As will be appreciated, in embodiments with a greater number if different sizes of VCOMs, the number of voltage sensing devices may increase. It should be noted that each gate line 104 may include a subset of pixels 102 from each VCOM. For example, one gate line 104 includes a subset 186 from the VCOM_A 130, a subset 188 from the VCOM_B 132, and a subset 190 from the VCOM_C 152.

Figure 8:
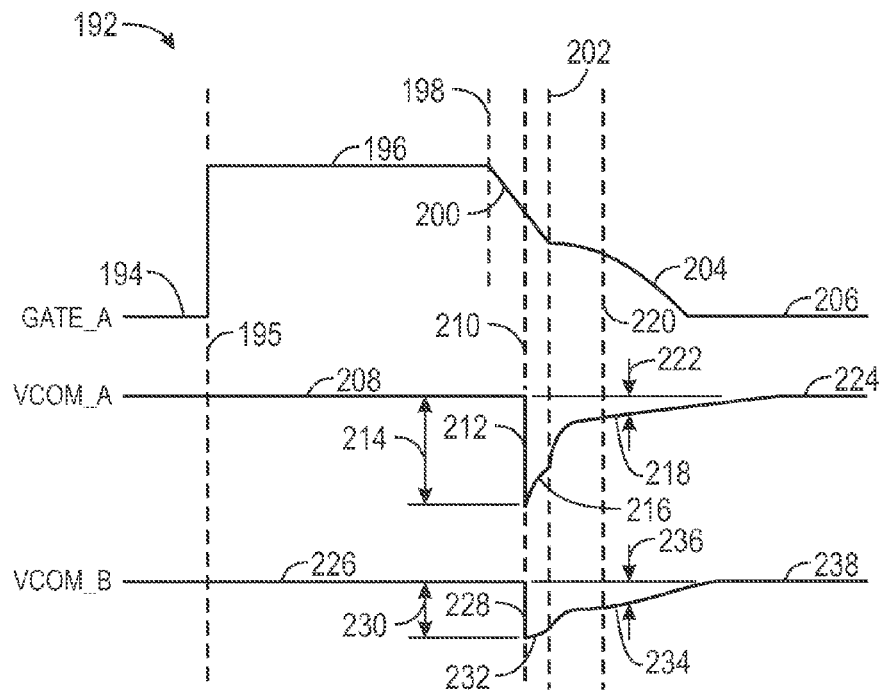
FIG. 8 is a timing diagram illustrating an effect of changing a gate clock fall time of the LCD, in accordance with an embodiment.

FIG. 8 relates to adjusting a gate clock fall time to decrease the voltage difference between VCOMs. FIG. 8 illustrates one embodiment of a timing diagram 192 that shows a reduction of the voltage difference 142 between VCOMs of the display 18 by controlling a rate that a voltage on a gate line 104 (e.g., GATE_A) is removed from pixels 102 to improve image quality of the display 18. As illustrated by segment 194, the gate line 104 may start in a logic low (deactivated) state. At a time 195, the gate line 104 may transition to a logic high (activated) state where it remains through segment 196. At a time 198, the gate line 104 may begin to transition toward the logic low state at a fixed rate, during segment 200. The fixed rate of transition may be a predetermined rate configured to be applied for a fixed period of time (e.g., until a time 202). At the time 202, the transition rate toward the logic low state may become variable (e.g., actively controlled) and may be based on the voltage difference 142, in order to decrease the voltage difference 142 between the VCOM_A 130 and the VCOM_B 132, as shown by segment 204. After the gate line 104 reaches the logic low state, the gate line 104 remains in the logic low state, as shown by segment 206.

In the present embodiment, a voltage is applied to the VCOM_A 130 during segment 208. At a time 210, a kickback voltage alters the voltage of the VCOM_A 130, as shown by segment 212. As illustrated, the voltage of the VCOM_A 130 may change by a voltage 214. The voltage of the VCOM_A 130 then begins to return to the voltage applied during segment 208, as shown by segments 216 and 218. Segment 216 corresponds to the rate that the gate line 104 is deactivated during segment 200, while segment 218 corresponds to the rate that the gate line 104 is deactivated during segment 204. At a time 220, the voltage of the VCOM_A 130 may vary from the voltage applied during segment 208 by a voltage 222. During segment 224, the voltage of the VCOM_A 130 may be approximately the same as the voltage applied during segment 208.

A voltage is applied to the VCOM_B 132 during segment 226. At the time 210, a kickback voltage alters the voltage of the VCOM_B 132, as shown by segment 228. As illustrated, the voltage of the VCOM_B 132 may change by a voltage 230. The voltage of the VCOM_B 132 then begins to return to the voltage applied during segment 226, as shown by segments 232 and 234. Segment 232 corresponds to the rate that the gate line 104 is deactivated during segment 200, while segment 234 corresponds to the rate that the gate line 104 is deactivated during segment 204. At the time 220, the voltage of the VCOM_B 132 may vary from the voltage applied during segment 226 by a voltage 236. During segment 238, the voltage of the VCOM_B 132 may be approximately the same as the voltage applied during segment 226.

In certain embodiments, the voltage applied to the VCOM_A 130 and the VCOM_B 132 may be approximately the same and, therefore, the voltage difference 142 between the VCOM_A 130 and the VCOM_B 132 during segments 208 and 226 may be approximately zero. Furthermore, the voltage difference 142 between the VCOM_A 130 and the VCOM_B 132 at the time 212 may be approximately the difference between the voltage 214 and the voltage 230. As previously described, such a voltage difference 142 may decrease the quality of an image on the display 18. Accordingly, the display 18 uses this voltage difference 142 to control the rate that the activation signal is removed from the pixels 102 (e.g., via the gate line 104) to decrease the voltage difference 142. Specifically, during segment 204 of the gate line 104, the display 18 uses the voltage difference 142 between the VCOM_A 130 and the VCOM_B 132 to change the rate that the activation signal is removed from the pixels 102. For example, the voltage difference 142 is reduced from its value at time 210 to a voltage difference 142 of the difference between the voltage 222 and the voltage 236 at the time 220. Further, during segments 224 and 238 the voltage difference 142 may be reduced to approximately zero.

Figure 9:
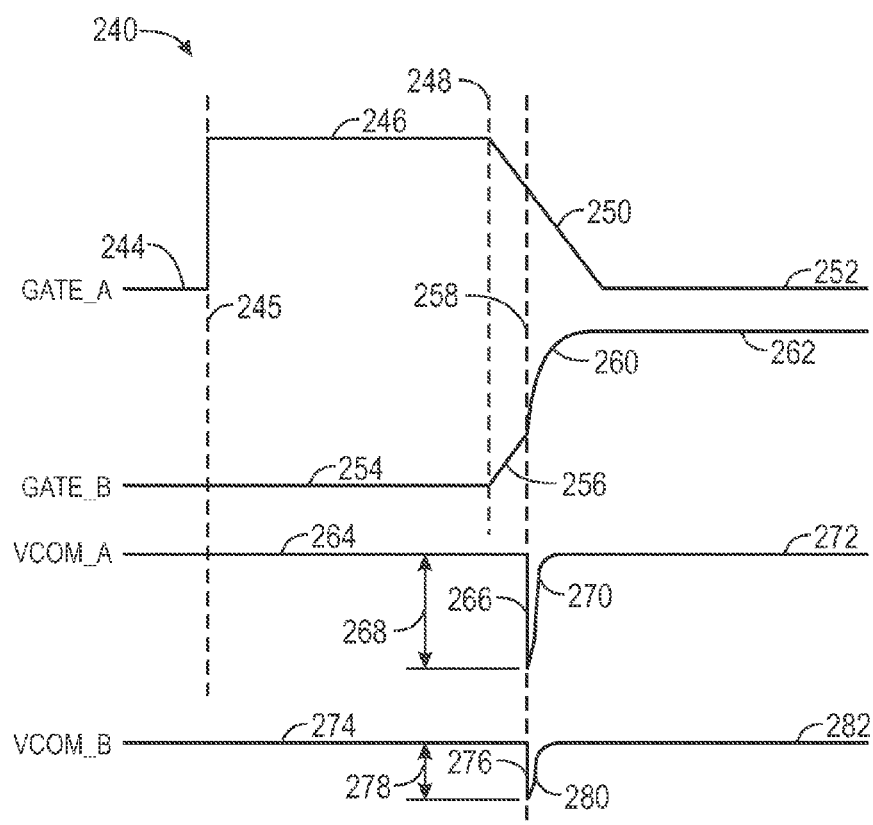
FIG. 9 is a timing diagram illustrating an effect of varying a gate clock overlap of the LCD, in accordance with an embodiment.

In some embodiments, the time that an activation signal is applied to pixels 102 is controlled to decrease the voltage difference between VCOMs. This may be referred to as gate clock overlap. FIG. 9 illustrates one embodiment of a timing diagram 240 that shows a reduction of the voltage difference 142 between VCOMs of the display 18 by controlling a time that a voltage on a second gate line 104 (e.g., GATE_B) is applied to pixels 102 to improve image quality of the display 18. As illustrated by segment 244, the first gate line 104 (e.g., GATE_A) may start in a logic low (deactivated) state. At a time 245, the first gate line 104 may transition to a logic high (activated) state where it remains through segment 246. At a time 248, the gate line 104 may transition toward the logic low state at a fixed rate, during segment 250. After the first gate line 104 reaches the logic low state, the first gate line 104 remains in the logic low state, as shown by segment 252.

As illustrated by segment 254, the second gate line 104 (e.g., GATE_B) may start in a logic low (deactivated) state. At the time 248, the second gate line 104 may transition toward a logic high (activated) state at a fixed rate, as shown by segment 256. The fixed rate of transition may be a predetermined rate configured to be applied for a fixed period of time (e.g., until a time 258). At the time 258, the transition rate toward the logic high state may become variable (e.g., actively controlled) and may be based on the voltage difference 142, in order to decrease the voltage difference 142 between the VCOM_A 130 and the VCOM_B 132, as shown by segment 260. After the second gate line 104 reaches the logic high state, the second gate line 104 remains in the logic high state, as shown by segment 262.

In the present embodiment, a voltage is applied to the VCOM_A 130 during segment 264. At the time 258, a kickback voltage alters the voltage of the VCOM_A 130, as shown by segment 266. As illustrated, the voltage of the VCOM_A 130 may change by a voltage 268. The voltage of the VCOM_A 130 then returns to the voltage applied during segment 264, as shown by segment 270. Segment 270 corresponds to the rate that the second gate line 104 is activated during segment 260. During segment 262, the voltage of the VCOM_A 130 may be approximately the same as the voltage applied during segment 264.

A voltage is applied to the VCOM_B 132 during segment 274. At the time 258, a kickback voltage alters the voltage of the VCOM_B 132, as shown by segment 276. As illustrated, the voltage of the VCOM_B 132 may change by a voltage 278. The voltage of the VCOM_B 132 then returns to the voltage applied during segment 274, as shown by segment 280. Segment 280 corresponds to the rate that the second gate line 104 is activated during segment 260. During segment 282, the voltage of the VCOM_B 132 may be approximately the same as the voltage applied during segment 274.

In certain embodiments, the voltage applied to the VCOM_A 130 and the VCOM_B 132 may be approximately the same and, therefore, the voltage difference 142 between the VCOM_A 130 and the VCOM_B 132 during segments 264 and 274 may be approximately zero. Furthermore, the voltage difference 142 between the VCOM_A 130 and the VCOM_B 132 at the time 258 may be approximately the difference between the voltage 268 and the voltage 278. As previously described, such a voltage difference 142 may decrease the quality of an image on the display 18. Accordingly, the display 18 uses this voltage difference 142 to control the rate and/or timing that the activation signal is applied to the pixels 102 (e.g., via the second gate line 104) to decrease the voltage difference 142. Specifically, during segment 260 of the second gate line 104, the display 18 uses the voltage difference 142 between the VCOM_A 130 and the VCOM_B 132 to change the rate that the activation signal is applied to the pixels 102. For example, the voltage difference 142 is reduced from its value at time 258 to a voltage difference 142 of approximately zero during segments 272 and 282.

To summarize, the examples of FIGS. 6-9 may generally describe adjusting the gate clock overlap and gate clock fall time as a function of the voltage difference between various VCOMs. However, it should be appreciated that the gate clock overlap and gate clock fall time may be calibrated at one time and the values of which stored as the operating parameters 129 in the storage 16 of the electronic device 10 and/or the nonvolatile memory 128 of the display 18. That is, rather than dynamically change the gate clock overlap and gate clock fall time operating parameters 129, these values may be set as static values selected to reduce or eliminate mura artifacts. These values may be adjusted according to the various techniques discussed further below.

Source Output Parking Voltage

Another operating parameter 129 that may be adjusted and programmed into the storage 16 and/or nonvolatile storage 128 is a source output parking voltage. Source output parking voltage refers to a voltage remaining on the source lines 106 when the display 18 temporarily operates in the touch mode rather than the display mode. In particular, it is believed that adjusting the source output parking voltages of the display 18 may adjust the leakage currents of the pixels 102. Adjusting the leakage current of the pixels 102 may, in turn, adjust the visibility of the mura artifact of the display 18. A further discussion of source output parking voltages may be found in U.S. Patent Application Ser. No. 61/655,667, "DEVICES AND METHODS FOR IMPROVING IMAGE QUALITY IN A DISPLAY HAVING MULTIPLE VCOMS," filed on Jun. 8, 2012, assigned to Apple, Inc., and incorporated by reference herein in its entirety. Examples describing the effect of adjusting the source output parking voltage are provided with reference to FIGS. 10 and 11.

Figure 10:
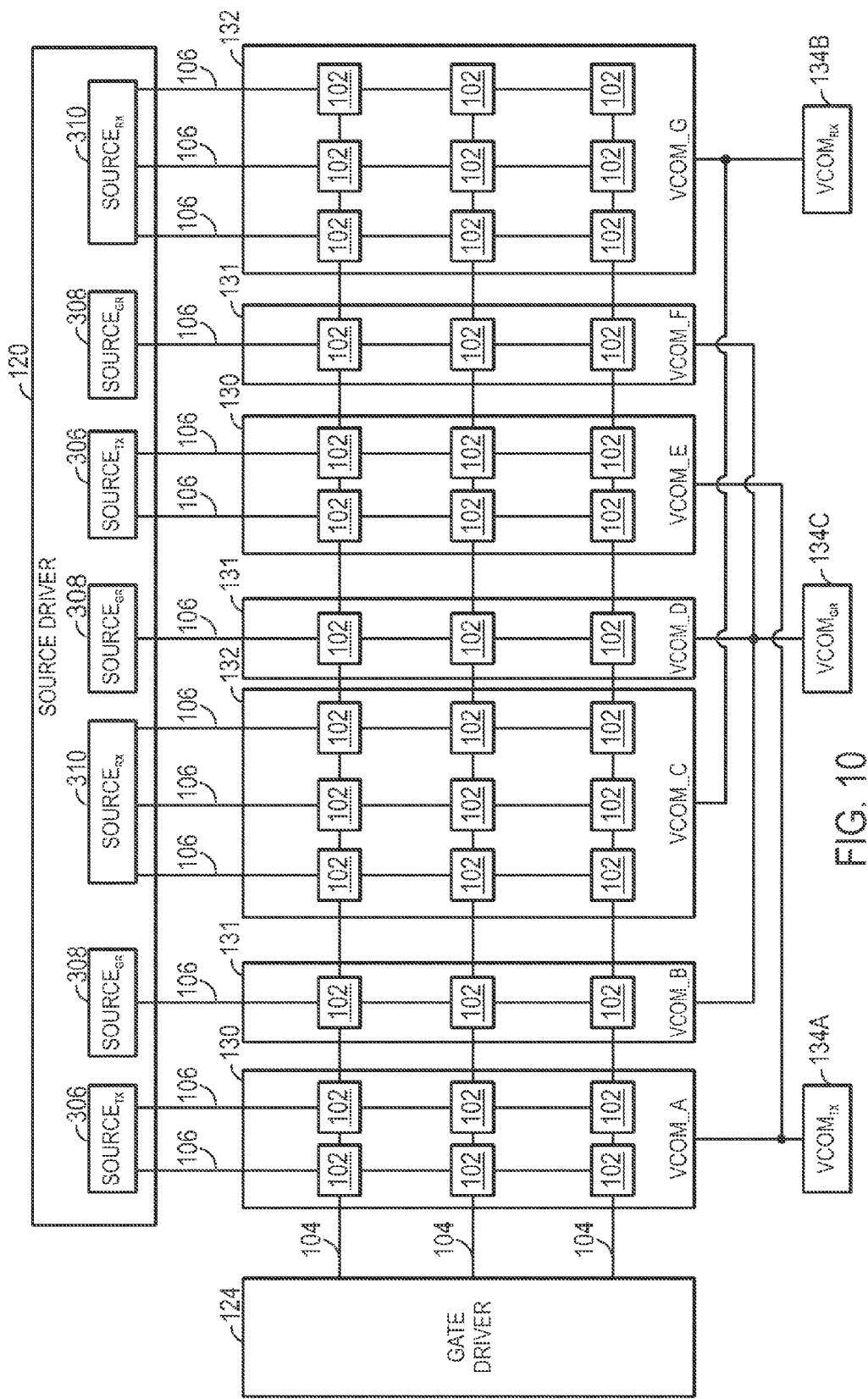
FIG. 10 is a block diagram of circuitry for controlling a source output parking voltage to improve image quality of the LCD, in accordance with an embodiment.

Namely, FIG. 10 generally represents one embodiment of a circuit diagram of components of the electronic device 10 for applying different signals to different VCOMs of the display 18 having multiple VCOMs to improve image quality of the display 18. In particular, the electronic device 10 includes a VCOM_A 130, a VCOM_B 131, a VCOM_C 132, a VCOM_D 131, a VCOM_E 130, a VCOM_F 131, and a VCOM_G 132. As illustrated, the VCOM_A 130, the VCOM_B 131, the VCOM_C 132, the VCOM_D 131, the VCOM_E 130, the VCOM_F 131, and the VCOM_G 132 each have multiple pixels 102 coupled thereon. As may be appreciated, the VCOMs may have any number of pixels 102 coupled thereon. Furthermore, there may be any suitable number of VCOMs of the display 18. It should be noted that the common electrodes 112 of the illustrated pixels 102 may be electrically coupled to their respective VCOM.

In certain embodiments, the VCOMs of the display 18 may be arranged into rows and columns. The rows and columns of the VCOMs may be used during a touch mode of the display for sensing touches of the display. For example, a touch driving signal (e.g., a low voltage AC signal) may be supplied to one or more rows of VCOMs. While the signal is supplied, a touch may be sensed using one or more columns of VCOMs. In the present embodiment, the VCOM_A 130 and the VCOM_E 130 may be part of a row of VCOMs. Accordingly, the VCOM_A 130 and the VCOM_E 130 may be electrically coupled together. Furthermore, the VCOM_A 130 and the VCOM_E 130 may be electrically coupled to a $VCOM_{TX}$ 134A configured to provide a touch driving signal to the row of VCOMs. As may be appreciated, the display 18 may include one or more $VCOM_{TX}$ 134A to drive the rows of VCOMs of the display 18.

The VCOM_C 132 and the VCOM_G 132 may be part of the columns of VCOMs of the display 18. For example, the VCOM_C 132 may be part of one column of VCOMs and the VCOM_G 132 may be part of another column of VCOMs. As illustrated, the VCOM_C 132 and the VCOM_G 132 may be electrically coupled together. Furthermore, the VCOM_C 132 and the VCOM_G 132 may be electrically coupled to a $VCOM_{RX}$ 134B configured to sense a touch of the display 18. As may be appreciated, the display 18 may include one or more $VCOM_{RX}$ 134B to sense touches of the display 18. For example, the display 18 may include one $VCOM_{RX}$ 134B for each column of VCOMs.

The display 18 may include VCOMs that function as guard rails configured to inhibit direct capacitive coupling (e.g., without a touch such as from a finger) from occurring between the rows and columns of VCOMs. As illustrated, the VCOM_B 131, the VCOM_D 131, and the VCOM_F 131 may all be guard rails. As illustrated, the VCOM_B 131, the VCOM_D 131, and the VCOM_F 131 may be electrically coupled together. Furthermore, the VCOM_B 131, the VCOM_D 131, and the VCOM_F 131 may be electrically coupled to a $VCOM_{GR}$ 134C. As may be appreciated, the display 18 may include one or more $VCOM_{GR}$ 134C that may provide signals to the guard rails.

The gate driver 124 is coupled to the gate lines 104 for activating and/or deactivating the gates 116 of the TFTs 108 of the pixels 102. Furthermore, the source driver 120 is coupled to the source lines 106 for supplying data signals to the sources 114 of the TFTs 108 of the pixels 102. As may be appreciated, the source driver 120 may supply data signals to pixels 102 based on the VCOM that the pixels 102 are coupled to. For example, the source driver 120 may supply data signals of a first voltage to pixels 102 of VCOM rows (e.g., $SOURCE_{TX}$ 306). Furthermore, the source driver 120 may supply data signals of a second voltage to pixels 102 of VCOM guard rails (e.g., $SOURCE_{GR}$ 308). Moreover, the source driver 120 may supply data signals of a third voltage to pixels 102 of VCOM columns (e.g., $SOURCE_{RX}$ 310). Although the $SOURCE_{TX}$ 306, the $SOURCE_{GR}$ 308, and the $SOURCE_{RX}$ 310 are illustrated as being part of the source driver 120, it should be noted that the $SOURCE_{TX}$ 306, the $SOURCE_{GR}$ 308, and the $SOURCE_{RX}$ 310 are illustrated to show that different signals may be supplied to different VCOMs of the display 12 and not that there are necessarily such devices within the source driver 120.

As illustrated, the VCOM_A 130, the VCOM_B 131, the VCOM_C 132, the VCOM_D 131, the VCOM_E 130, the VCOM_F 131, and the VCOM_G 132 may not physically be the same size. Accordingly, the VCOM_A 130, the VCOM_B 131, the VCOM_C 132, the VCOM_D 131, the VCOM_E 130, the VCOM_F 131, and the VCOM_G 132 may have resistive differences. In certain embodiments, the VCOM_A 130 and the VCOM_E 130 may be approximately the same size. Furthermore, the VCOM_C 132 and the VCOM_G 132 may be approximately the same size. Moreover, the VCOM_B 131, the VCOM_D 131, and the VCOM_F 131 may be approximately the same size.

Figure 11:
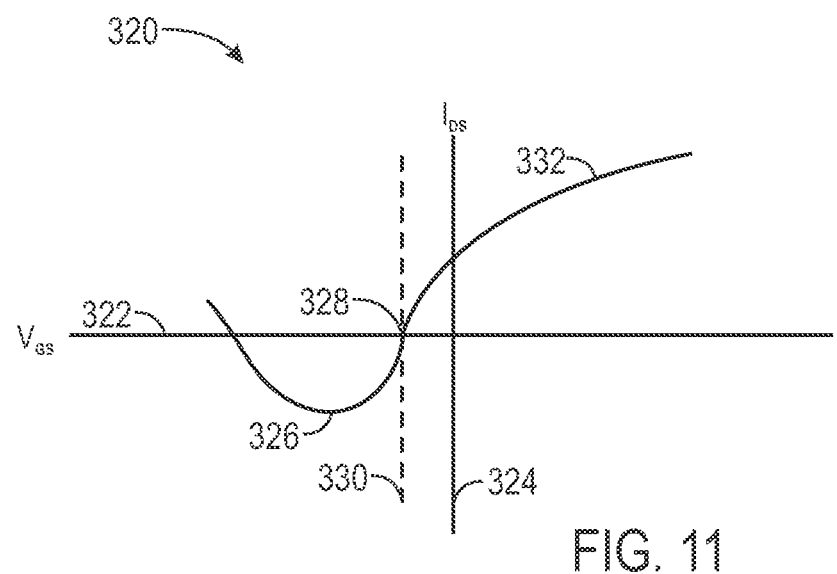
FIG. 11 is an I-V curve showing leakage currents of a thin film transistor (TFT) of a pixel of the LCD that may be adjusted using the source parking voltages as shown in FIG. 10.

During operation, the display 18 may alternate between a display mode and a touch mode. During the display mode, the display 18 receives image data and provides data signals to pixels 102 to store the image data on the pixels 102. During the touch mode, the display 18 provides a touch driving signal and senses touches that occur. As may be appreciated, when the touch driving signal is applied to the display 18, a gate-to-source voltage of the TFTs 108 of the pixels 102 may be modified, which may result in an increased leakage current (e.g., drain-to-source current) of the TFTs 108. FIG. 11 is a diagram 156 illustrating a relationship between a gate-to-source voltage 158 of a TFT 108 and a drain-to-source current 160 of the TFT 108.

Specifically, the drain-to-source current 160 is negative during a segment 162. At the end of segment 162, the drain-to-source current 160 reaches zero, at point 164. The gate-to-source voltage 158 at point 164 is indicated by a voltage 166 which is a negative voltage. During a segment 168, the drain-to-source current 160 is positive. Accordingly, if the gate-to-source voltage 158 were to fluctuate about the axis 160 based on a touch driving signal (e.g., a low voltage AC signal), the drain-to-source current 160 would fluctuate between a low positive value and a high positive value, resulting in a potential for high leakage, which in turn may decrease the quality of the image of the display 18. However, if the gate-to-source voltage 158 were to fluctuate about an axis formed by the voltage 166, the drain-to-source current 160 would fluctuate between a low negative value and a low positive value, resulting in lower leakage and improving the quality of the image of the display 18. Accordingly, voltages are applied to the source lines 106 to change the gate-to-source voltage 158 and thereby shift the axis related to the drain-to-source current 160 fluctuations.

In certain embodiments, voltages may be applied to the source lines 106 as part of the display mode and remain applied during the touch mode until the display mode resumes. Specifically, data may be stored on the pixels 102 of the display 18 line by line during the display mode until all lines of pixels 102 have data stored on them. For example, if the display 18 were to have 960 lines of pixels 102, during the display mode all 960 lines of pixels 102 may have data stored on them. In certain embodiments, as part of the display mode, the display 18 may act as if it contains a 961st line of pixels 102 (e.g., a virtual line). For the 961st line of pixels 102, voltages are applied to the source lines 106 just as when other lines of pixels 102 store data; however, the gate lines 104 are not activated (e.g., remain deactivated) so that data is not stored on the pixels 102. Furthermore, the voltages applied to the source lines 106 remain after the display mode ends and through the touch mode until the display mode begins again. As such, the voltages applied to the source lines 106 may be considered "parked."

As previously discussed, the voltages applied to the source lines 106 may vary based on the VCOMs that the source lines 106 provide signals to. The voltages may vary in order to tune each set of pixels 102 coupled to a single VCOM so that the TFTs 108 of the VCOM have a minimum amount of leakage current. The difference in voltage between different VCOMs may be due in part to the size of the VCOMs, the number of pixels 102 coupled to the VCOMs, and so forth. In one embodiment, the voltage applied to the source lines represented by SOURCE$_{TX}$ 306 may be approximately a gray 255 voltage, the voltage applied to the source lines represented by SOURCE$_{GR}$ 308 may be approximately a gray 127 voltage, and the voltage applied to the source lines represented by SOURCE$_{RX}$ 310 may be approximately a gray 0 voltage. In another embodiment, the voltage applied to the source lines represented by SOURCE$_{TX}$ 306 may be approximately a gray 255 voltage, the voltage applied to the source lines represented by SOURCE$_{GR}$ 308 may be approximately a gray 204 voltage, and the voltage applied to the source lines represented by SOURCE$_{RX}$ 310 may be approximately a gray 192 voltage. In other embodiments, the voltages applied to the source lines represented by SOURCE$_{TX}$ 306, SOURCE$_{GR}$ 308, and SOURCE$_{RX}$ 310 may be tuned to any suitable voltage. Accordingly, the leakage current of TFTs 108 of the pixels 102 may be reduced and the image quality of the display 18 may be improved.

The particular source output parking voltages applied may be selected and stored as operating parameters 129 in the storage 16 and/or the nonvolatile memory 128. With different source output parking voltages, the mura artifacts due to the different VCOMs may become more or less pronounced.

Differential VCOM Resistance

It is believed that the differential bias voltages that may occur on the different VCOMs may be due at least in part to different transient voltage perturbations that occur on the VCOMs. Changing the RC time constants of the VCOMs thus may impact these transient voltage perturbations. Thus, another of the operational parameters 129 of the display 18 that may be changed, in some embodiments, is a differential VCOM resistance value or differential capacitance value. It should be appreciated that, as used in this document, references to an operating parameter 129 relating to VCOM resistance should be understood to include, additionally or alternatively, varying VCOM capacitance. A further discussion of differential VCOM resistance may be found in U.S. Patent Application Ser. No. 61/657,671, "Differential VCOM Resistance or Capacitance Tuning for Improved Image Quality," filed on Jun. 8, 2012, assigned to Apple, Inc., and incorporated by reference herein in its entirety. The following discussion relating to FIGS. 12-14 will generally describe how the VCOM resistance may affect the appearance of mura artifacts.

Figure 12:
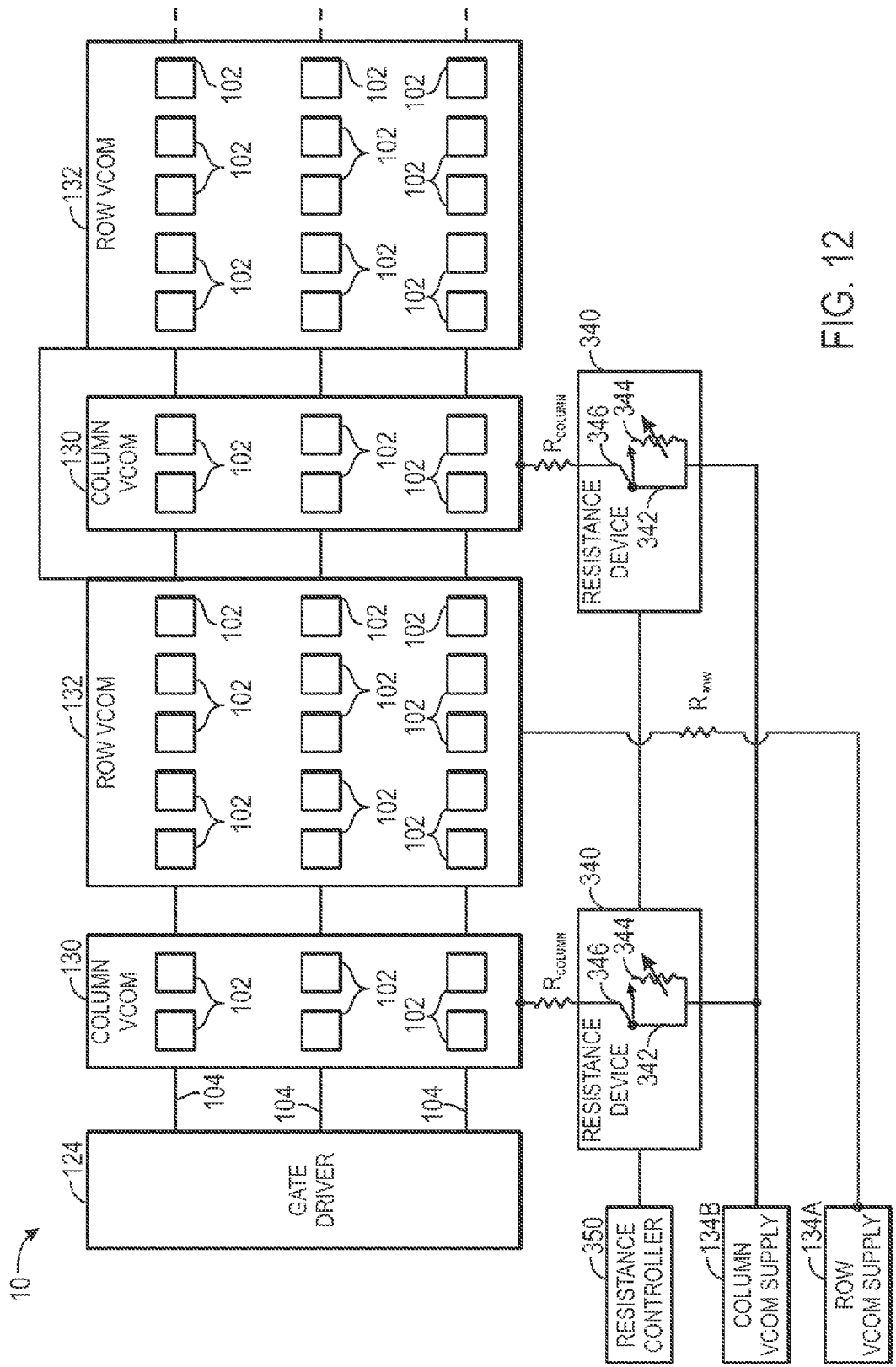
FIG. 12 is a block diagram illustrating circuitry for adjusting resistances of VCOMs of the LCD to improve image quality, in accordance with an embodiment.

As mentioned above, the display 18 may have any suitable number of VCOMs and the VCOMs may vary in size. FIG. 12 generally represents a diagram of circuitry of the electronic device 10 capable of reducing variation in voltage perturbation between the column VCOMs 130 and the row VCOMs 132 of the display to improve image quality of the display 18. Specifically, in the present embodiment, the display 18 includes a column VCOM 130 and a row VCOM 132. Each of the column VCOM 130 and the row VCOM 132 may include a plurality of pixels 102, as shown. Further, the display 18 may include a plurality of row VCOMs 132 and a plurality of column VCOMs 130. The row VCOMs 132 may be coupled to each other via a line such that each row VCOM 132 shares the same voltage level. The column VCOMs 130 may be individually coupled to the VCOM source 134. Although not shown in FIG. 12, other VCOMs may also be present (e.g., "guard rail" VCOMs 131 between the column VCOMs 130 and the row VCOMs 132).

At least partially due to the configuration of the row VCOMs 132—namely, that the row VCOMs 132 are in line with the gate lines 104—the row VCOMs 132 may experience greater interference from voltage changes in the gate line 104 due to TFT gate deactivation. Since each of the column VCOMs 130 may extend down the display 18, and thus only shares a relatively small part its total area with a given gate line 104, the column VCOMs 130 may experience comparatively less. Moreover, the column VCOMs 130 and the row VCOMs 132 may have different inherent resistances (e.g., Rcolumn and Rrow) between respective voltage supplies 134B and 134A, as well as different capacitances between the gate lines 104 (e.g., Cgc values associated with the VCOMs 130 and 132). The effect of these different VCOM characteristics, as well as different amounts of exposure to the gate lines 104, may produce different voltage perturbations on the column VCOMs 130 and the row VCOMs 132.

Since different voltage perturbations could produce image artifacts, differences in voltage perturbations may be mitigated by adjusting the resistance(s). As will be discussed below, increasing the column VCOM 130 resistance may cause the corresponding time constant of the voltage perturbation on the column VCOM 130 to be extended. Ordinarily, increasing a resistance is considered problematic. Indeed, an increased resistance can result in lower power efficiency and increased heat waste. In this case, however, increasing the resistance may reduce or eliminate image artifacts.

As such, column VCOMs 130 may be coupled to a resistance device 340. In the example of FIG. 12, the resistance device 340 includes a non-resistive path 342 and a resistive path 344 selectable by a switch 346. A resistance controller 350 may cause the resistance device 340 to switch between the resistive path 344 and the non-resistive path 342. The resistance controller 350 may be a separate component of the display 18 or may be integrated into other components of the display 18 (e.g., display or touch driver circuitry). In some embodiments, the resistance controller 350 may switch to the resistive path 344 during a display mode and to the non-resistive path 342 during a touch screen mode of the display 18. In other embodiments, only a resistive path 344 may be employed. In these embodiments, the resistance controller 350 may be absent.

In any case, the resistive path 344 may add resistance using any suitable resistive elements. These may include a resistor of a single value, a resistor that may be set or programmed during the fabrication of the display 18, or a variable resistance device (e.g., a resistor ladder). Additionally or alternatively, the resistance device 340 may include a capacitor. Such a capacitor may vary the time constant of the column VCOMs 130 in a similar manner as the additional resistance. Moreover, the column VCOMs 130 may be coupled to different resistance devices 340 with different resistance values. In certain embodiments, some column VCOMs 130 may be coupled to resistance devices 340 and some column VCOMs 130 may not be coupled to resistance devices 340.

Moreover, in some embodiments, the resistance controller 350 may do more than just control the switching of the resistance device 340 between the resistive path 344 and the non-resistive path 342. Indeed, the resistance controller 350 may, additionally or alternatively, control the resistance of the resistive path 344. For example, the resistive device(s) of the resistive path 344 may be chosen to provide a range of possible resistance values. The resistance controller 350 may tune the resistance of the resistive path 344 to reduce or eliminate image artifacts caused by variations in voltage perturbation.

Figure 13:
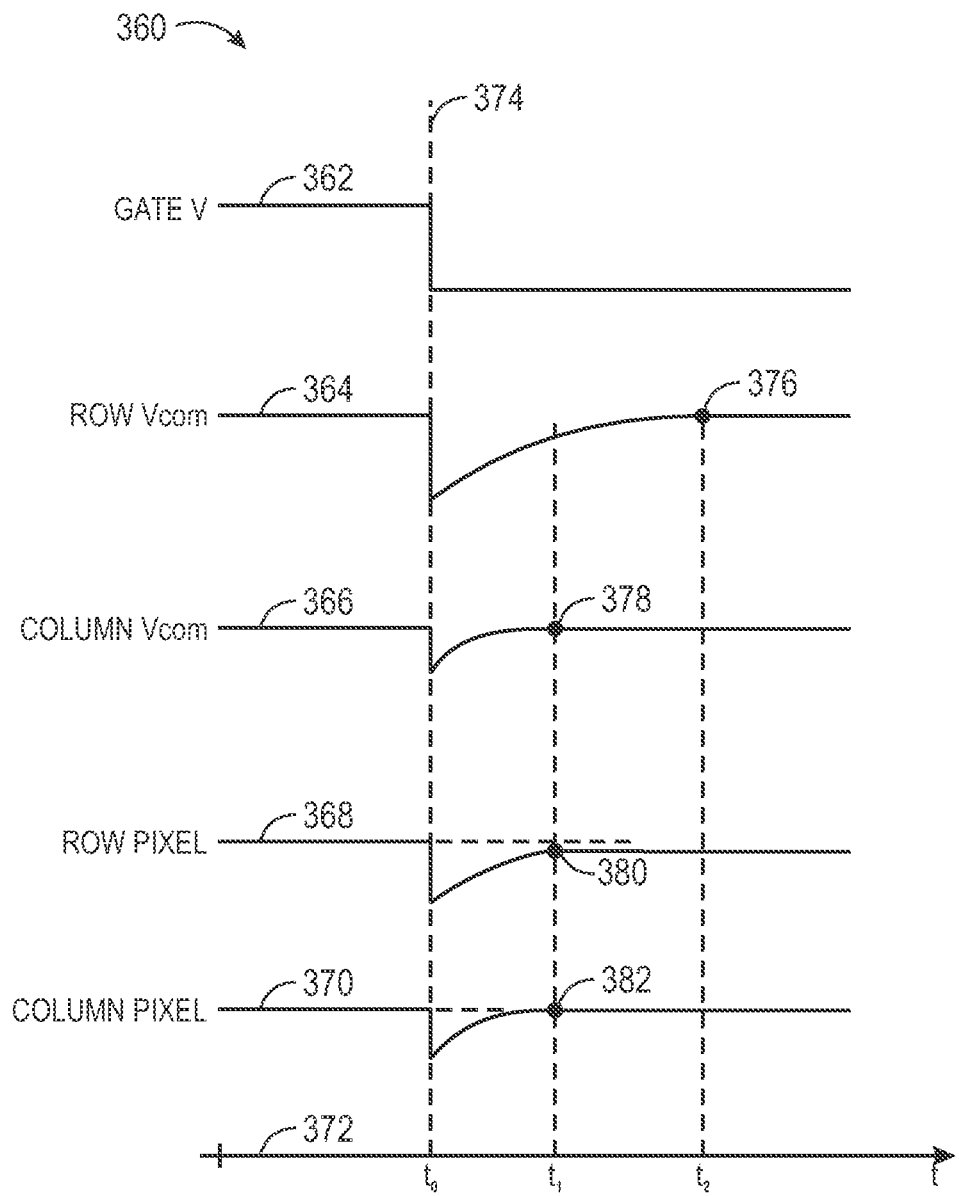
FIG. 13 is a timing diagram illustrating voltage changes in certain display elements caused by TFT gate deactivation when the disclosed techniques are not employed.
Figure 14:
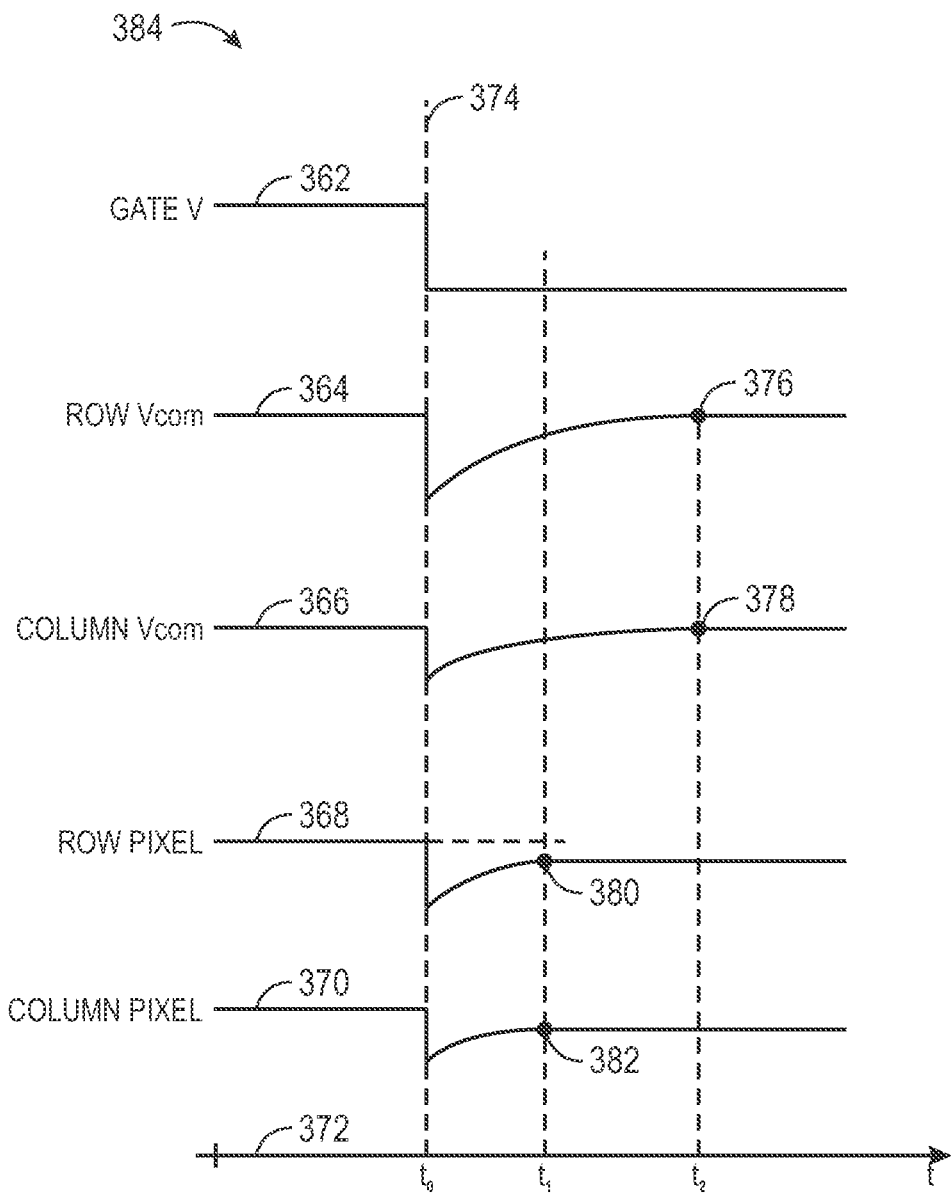
FIG. 14 is a timing diagram illustrating voltage changes in certain display elements caused by TFT deactivation after applying additional resistance to certain VCOMs, thereby improving image quality, in accordance with an embodiment.

FIGS. 13 and 14 illustrate the effect of reducing the voltage perturbation differences between the column VCOMs 130 and the row VCOMs 132. Namely, FIG. 13 represents a timing diagram when the present techniques are not applied, and FIG. 14 represents a timing diagram when the present techniques are applied.

FIG. 13 illustrates voltage levels 360 of the row VCOM 132 and the column VCOM 132 in response to TFT gate deactivation with respect to time when an additional resistance on the column VCOM 130 is not employed. TFT gate deactivation is illustrated by a gate voltage curve 362, in which the voltage in the TFT gate line 104 drops at $t_0$, signifying the point of TFT gate deactivation 374. Accordingly, due to capacitive coupling between the gate line 104 and the VCOMs 130 and 132, a voltage of the row VCOM (line 364) may also exhibits a transient drop in voltage at $t_0$ as well. The row VCOM 132, due to its configuration and physical relation to the gate line, may experience a rise time of $t_2-t_0$ in order to return to its original voltage value at $t_2$ (point 376). A voltage in the column VCOM (line 366) may experience a less dramatic voltage drop at $t_0$, in response to TFT gate deactivation 374. As such, the column VCOM 130 may return to its original voltage (point 378) faster than the row VCOM 132, at $t_1$.

A voltage in the row pixel (line 368), which is coupled to the row VCOM 132, may experience a similar drop in voltage level. As such, the row pixel voltage 368, which generally determines how much light is shown by the pixel, would not return to its original value until $t_2$. In the example of FIG. 13, however, the TFT 108 may completely open and prevent any changes in any pixels 102 after time $t_1$. Thus, the row pixel voltage 368 does not ever fully return to its programmed value, but instead stops at the voltage level it has reached by time $t_1$ (point 380). Meanwhile, a voltage in the column pixel (line 370) may experience a voltage drop and rise time similar to that of the column VCOM (line 378). The column pixel thus may return to its original value (point 382) at $t_1$. That is, the column pixel (line 370) may return to its original value faster than the row pixel (line 368). As a result, the variation in voltage perturbation between row VCOM (line 364) and column VCOM (line 366) may result in different programmed values in row pixels (point 380) and column pixels (point 382) even when the values should be the same. This may be seen on the display 18 as vertical striping artifacts when the column VCOMs 130 extend vertically down the display 18.

The rise time of the column pixel (line 370) may be altered by altering the resistance of the column VCOM 130. Specifically, the rise time of the column VCOM 130, and thus column pixel, may be increased by increasing the resistance of the column VCOM 130. As such, the resistance device 340 described above and illustrated in FIG. 12 may be chosen or tuned to a resistance that increases the rise time of the column VCOM to match that of the row VCOM. Thus, the variation in voltage perturbation between the column pixel and the row pixel caused by TFT deactivation may be largely reduced and/or eliminated.

FIG. 14 illustrates the voltage levels 384 of the row VCOM (line 364) and the column VCOM (line 366), in which the column VCOM 130 is coupled to the resistance device 340 shown in FIG. 13. As illustrated, the gate voltage (line 362) drops at the point of TFT gate deactivation 374. Likewise, the row VCOM voltage (line 364) and column VCOM voltage (line 366) drop as well, due to the capacitive coupling between the VCOMs 130 and 132 and the gate line 104. The row VCOM 132 experiences a rise time of $t_2$ in order to return to its original voltage (point 376). The column VCOM 130, due to it its added resistance from the resistance device 340, may also experience a rise time of $t_g$ in order to return to its original voltage level (point 378). Accordingly, the row pixel voltage (line 368) and column pixel voltage (line 382) experience correspondingly similar rise times in response to TFT gate deactivation. In some embodiments, the voltage drops may also be similar, but may not be in all cases. As such, both the row pixel voltage (line 370) and the column pixel voltage (line 382) may be stopped at the same voltage level when the TFT 108 completely opens and the row pixels (line 368) and column pixels (line 370) stabilize. Thus, display errors and artifacts attributed to variation in voltage perturbation between row VCOMs 132 and column VCOMs 130 may be largely reduced and/or eliminated.

As mentioned, the resistance device 340 may be switched on when the display is in display mode. In certain embodiments, the resistance controller 350 may detect that the display 18 is in the display mode. The resistance controller 350 may detect that the display 18 is in the display mode by sensing a signal indicative of the display 18 being in the display mode. The resistance controller 350 may connect the resistive path 344 in response to detecting the display mode. Thus, the column VCOM 130 may be coupled to the resistance path 344 and take on a higher resistance value. As discussed, this may allow the column VCOM 130 rise time to generally match that of the row VCOM 132. In other embodiments, this may allow the column VCOM 130 rise time to be lengthened such that the ultimate voltage programmed in the column pixels 102 is the same as that of the row pixels 102 when the same source or data voltage is provided.

Since the resistance device 340 may not be needed when the display 18 is in touch mode, the resistance controller 350 may be configured to detect when the display 18 is in the touch mode. As such, the resistance controller 166 may connect to the non-resistive path 342 in response to detecting the touch mode, decoupling the column VCOM 130 from the resistive path 344. The resistance controller 350 may continue to detect when the display 18 is in the display mode or touch mode, and switch the resistance device 340 accordingly.

In this way, variable resistances applied to the VCOMs of the display 18 (as stored as the operating parameters 129 in the nonvolatile memory 128) may reduce or eliminate mura artifacts. This and any other suitable operating parameters 129, including gate clock overlap, gate clock fall time, and/or source output parking voltage may be used to reduce or eliminate mura artifacts (e.g., VSFOMs) due to differential VCOM characteristics.

Calibration of the Display and Programming of the Operating Parameters

Figure 15:
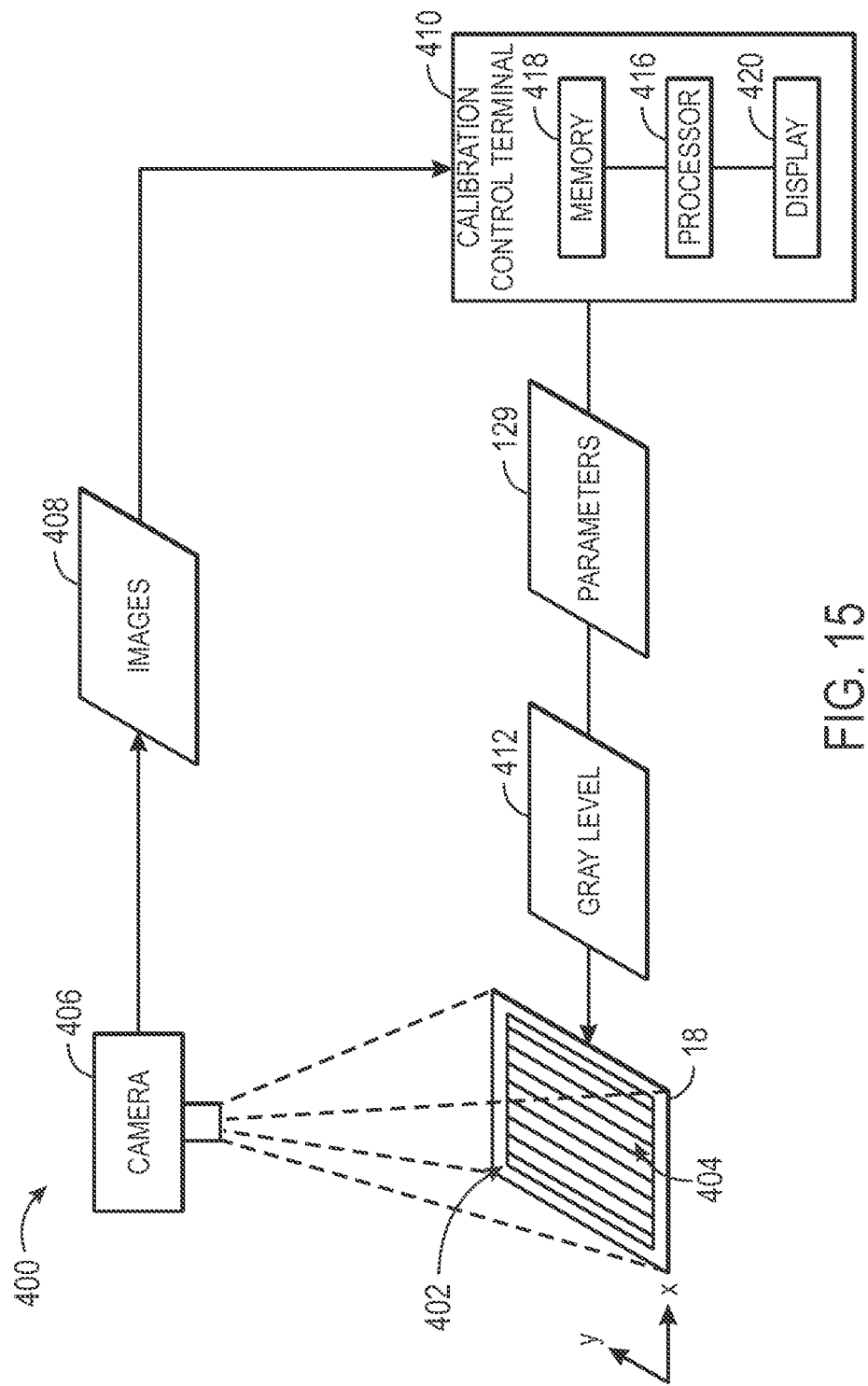
FIG. 15 is a block diagram of a system for calibrating the LCD to reduce or eliminate certain muras, in accordance with an embodiment.

The various operating parameters 129 discussed above can be used to reduce or eliminate muras, such as vertical stripe features of merit (VSFOMs) in the display 18. A calibration control system 400, as shown by FIG. 15 represents one example of a system to reduce or eliminate mura artifacts of the display 18. In the example of FIG. 15, a peripheral area 402 and an active area 404 of the display 18 are pictured. A coordinate system appearing in FIG. 15 includes a y axis and an x axis. A mura artifact on the display 18 includes alternating light and dark lines parallel to the y axis.

A camera 406 may capture at least a portion of the active area 404 where mura artifacts may be to produce at least one image 408. The camera 406 may be any suitable digital imaging device that can capture the artifact on the display 18 in sufficient contrast. It is believed that less contrast may be needed when the system 400 relies on a human operator than when the system 400 calibrates the display 18 automatically. As such, when the system 400 calibrates the display 18 automatically, the camera 406 may be a camera that can capture a higher dynamic range. For example, it is believed that the contrast between elements of the mura artifact may differ by less than one-fifth of a gray level and still remain visible. To capture this contrast when operating in an automatic mode rather than being controlled by a human operator, the camera 406 may capture 12 bits of dynamic range or more. When controlled by a human operator, a less expensive camera 406 of lower dynamic range may be used.

A calibration control terminal 410, which may be any suitable computer system, may receive the images 408 from the camera 406. The calibration control terminal 410 may control the display 18 according to a programmed algorithm or under the control of a human operator. As will be discussed below, the calibration control terminal 410 may initially select a gray level 412 for the pixels of the display 18 to display. The gray level 412 may be displayed by at least those pixels captured in the images 408. Using the images 408 as feedback, the calibration control terminal 410 and/or its human operator may adjust the parameters 129 of the display 18 such that mura artifacts are reduced and/or eliminated.

As mentioned above, the calibration control terminal 410 may be any suitable electronic device or computer system that can control the display 18 in the manner shown in FIG. 15. As such, the calibration control terminal 410 may include any suitable processor 416 and memory and/or storage 418. The processor 416 may carry out instructions encoded in the memory and/or storage 418 according to the techniques discussed below. When the calibration is performed in a generally automatic fashion, a display 420 may or may not be present. When controlled by a human operator, the human operator may view the images 408 on the display 420 as feedback to adjustments to the operating parameters 129.

The calibration of system 400 of FIG. 15 may amplify the contrast in the images 408 to make the mura artifact of the display 18 more clearly visible. A flowchart 430 of FIG. 16, for example, describes one manner in which the display 18 may be calibrated to reduce or eliminate mura artifacts. The flowchart 430 of FIG. 16 may be carried out automatically or by a human operator. The flowchart 430 may begin when the pixels of the display 18 are set to a gray level sufficient to produce contrasting mura artifacts (block 432). Any suitable gray level may be employed. It is believed that a gray level of G63 out of a range of possible gray levels of G0 to G255 will produce the highest amount of contrast in the mura artifact. In some embodiments, the gray level may be any value between gray levels of around G40 and G80, depending on the particular susceptibility to these gray levels to the mura artifacts. In some embodiments, the gray level selected may be less than G127.

The camera 406 may obtain images 408 of the display 18 (block 434). The calibration control terminal 410 may determine an average luminance of the display panel 18 in the image(s) 408 (block 436). The calibration control terminal 410 then may amplify the image(s) 408 around the average luminance(s) (block 438). When these amplified images 408 are displayed on the display 420, a human operator may be able to more clearly see the effects of changing the operating parameter(s) 129 of the display.

Figure 16:
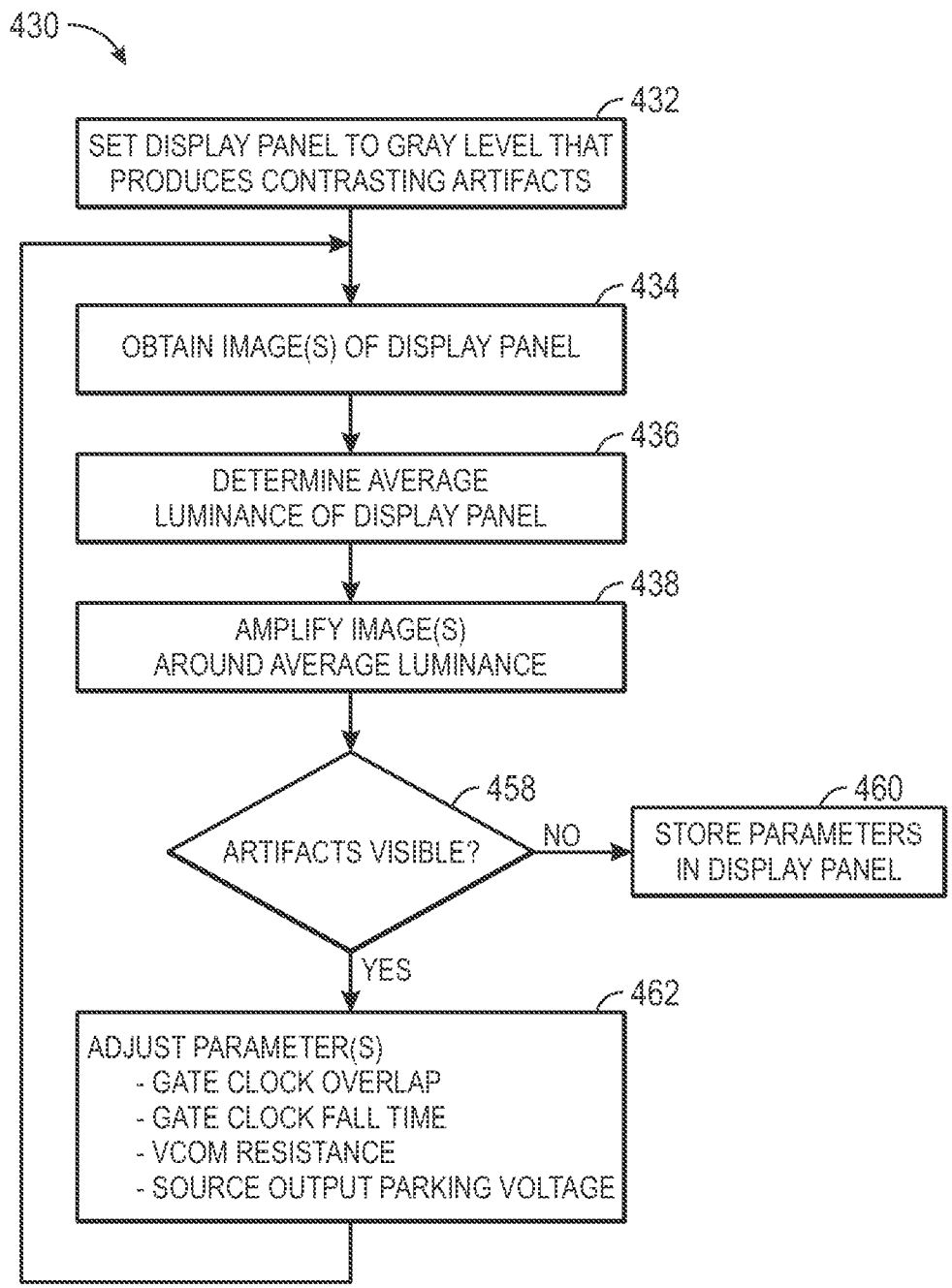
FIG. 16 is a flowchart of a method for reducing or eliminating the muras using the system of FIG. 15, in accordance with an embodiment.
Figure 17:
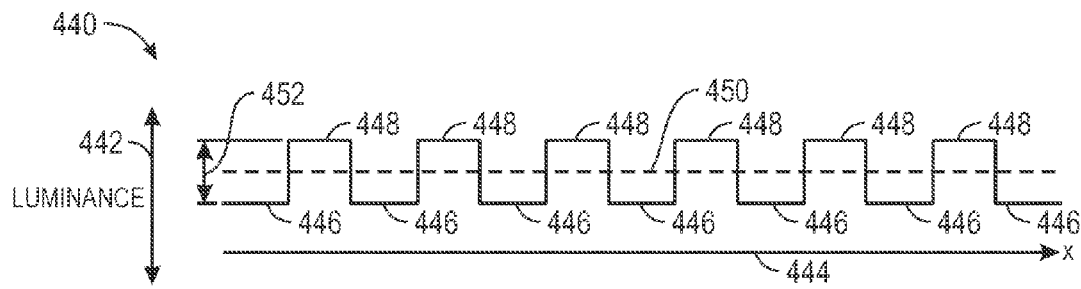
FIGS. 17 and 18 are luminance plots of muras of the LCD, as used in the method of FIG. 16, in accordance with an embodiment.
Figure 18:
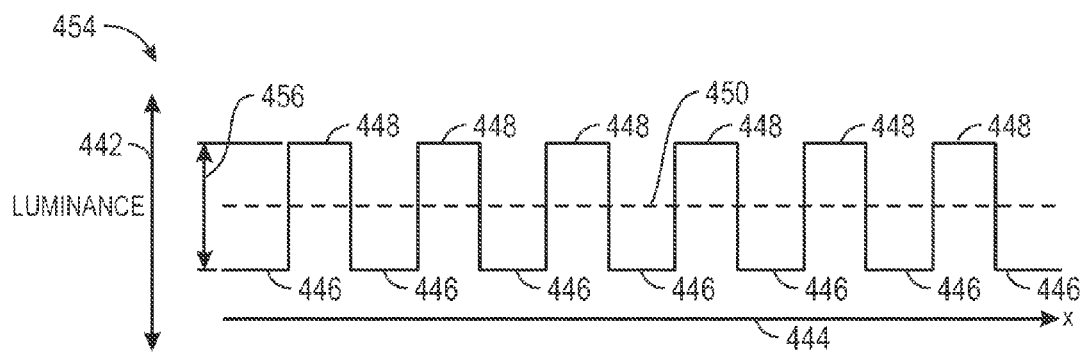

Before continuing further in the flowchart 430 of FIG. 16, the reader is directed to FIGS. 17 and 18, which generally illustrate the effect of amplifying the image(s) 408. In the example of FIG. 17, which may represent the image(s) 408 at block 436, a luminance diagram 440 shows luminance (ordinate 442) of the display 18 along the x axis (abscissa 444) of the display 18. The luminance varies across the width of the display 18 due to vertical stripes of the mura, which may be seen as areas of low luminance 446 and areas of high luminance 448. These areas of low luminance 446 and areas of high luminance 448 may be averaged to obtain an average luminance 450. A contrast may be visualized as a luminance difference 452 between the areas of low luminance 446 and the areas of high luminance 448.

FIG. 18 generally represents a luminance of the images 408 after block 438. In FIG. 18, a luminance diagram 454 shows that the areas of low luminance 446 and the areas of high luminance 448 have been amplified in relation to the average luminance 450. As such, a luminance difference 456 is much greater. With this higher contrast, a human operator and/or the calibration control terminal 410 may more easily discern the mura artifacts.

Returning to the flowchart 430 of FIG. 16, using the amplified images 408, a human operator and/or the calibration control terminal 410 may determine whether any mura artifacts are visible (decision block 458). If not, the current operating parameters 129 being supplied to the display 18 may be programmed in the non-volatile memory 128 of the display 18 (block 460).

If any mura artifacts remain visible, the human operator and/or the calibration control terminal 410 may adjust one or more operating parameters 129 (block 462). As mentioned above, the operating parameter(s) 129 may include a gate clock overlap, a gate clock fall time, a VCOM resistance, a source output parking voltage, and/or any other suitable operating parameters that affect the appearance of the mura artifacts. As the parameters are adjusted (block 462), the images 408 may continue to be obtained (block 434), the luminances of each averaged (block 436), and amplified (block 438) as discussed above. The operating parameters 129 may continue to be adjusted until the mura artifacts are no longer visible.

Figure 19:
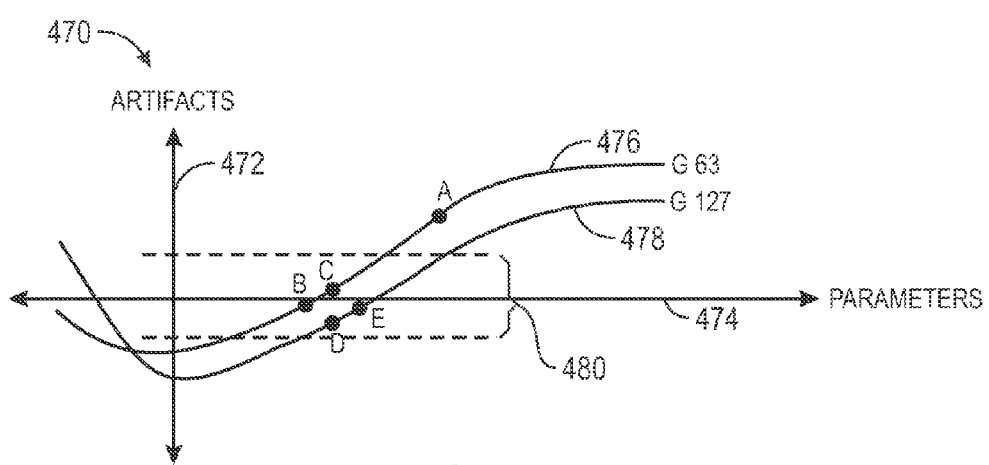
FIG. 19 is a plot comparing artifacts to operational parameters for two gray levels, with points associated with a first method for correcting for certain muras, in accordance with an embodiment.
Figure 20:
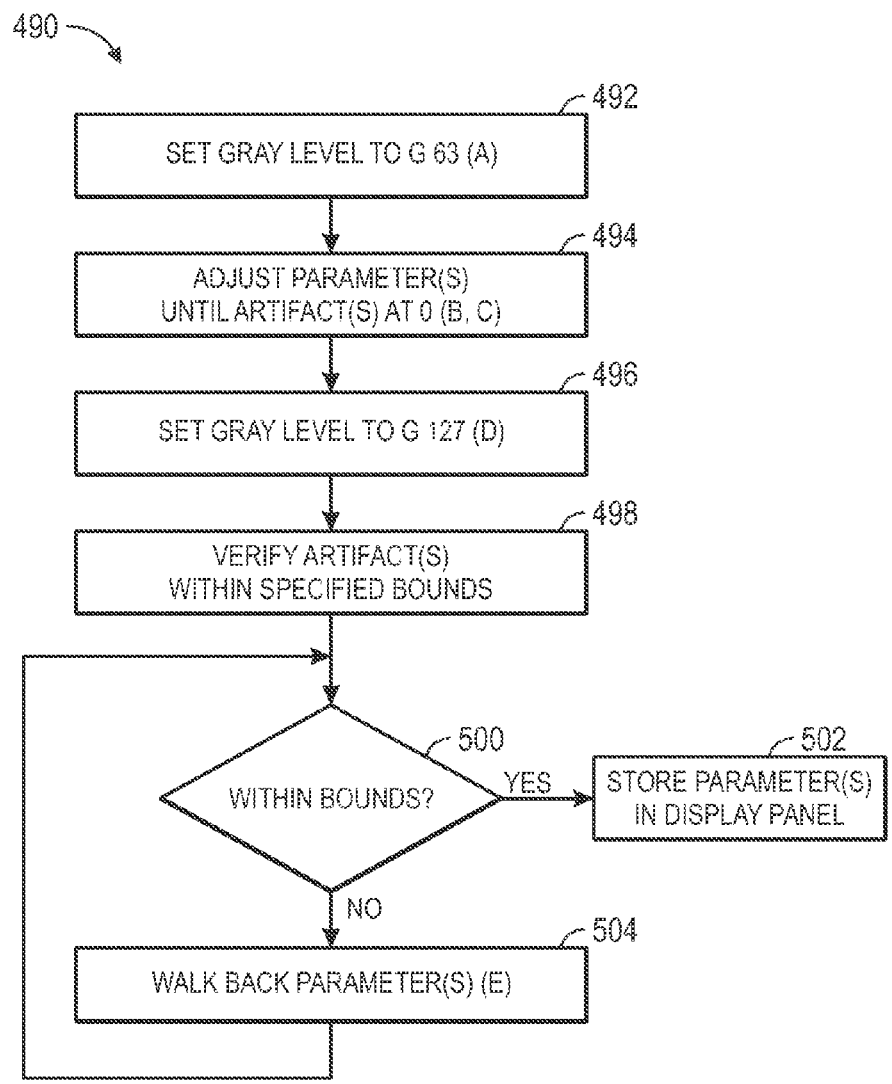
FIG. 20 is a flowchart of a method for reducing or eliminating certain muras as generally illustrated in FIG. 19, in accordance with an embodiment.
Figure 21:
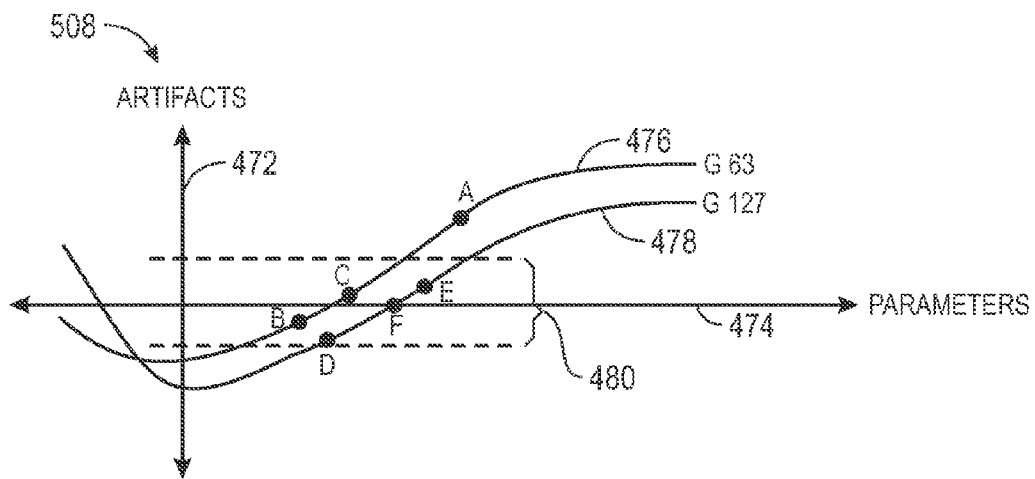
FIG. 21 is a plot comparing artifacts to operational parameters for two gray levels, with points associated with a second method for correcting for certain muras, in accordance with an embodiment.
Figure 22:
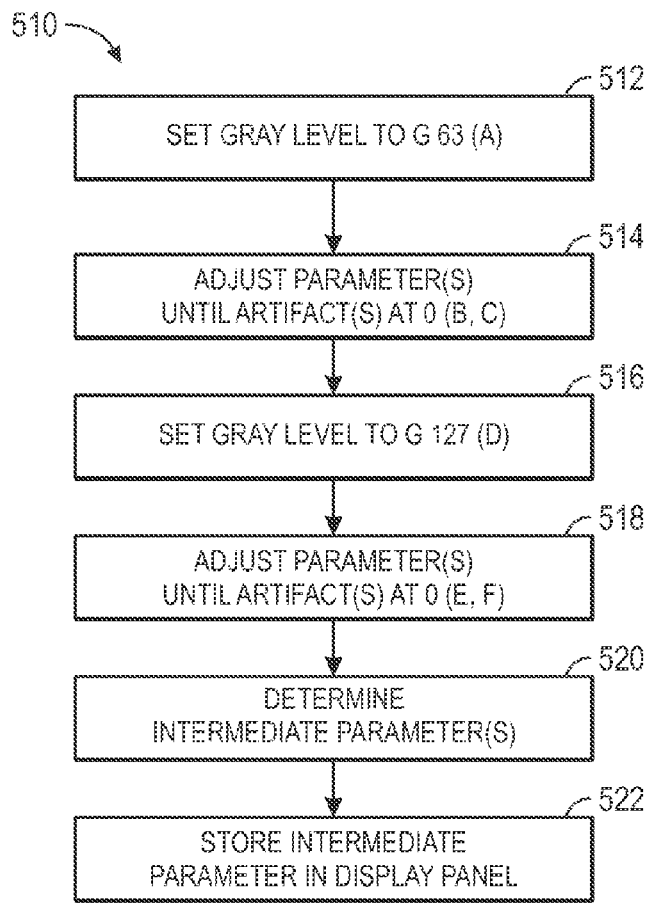
FIG. 22 is a flowchart of a method for reducing or eliminating certain muras as generally illustrated in FIG. 21, in accordance with an embodiment.

With or without amplifying the images 408 as in the method 430 of FIG. 16, the calibration control terminal 410 and/or a human operator may calibrate the display 18. For example, the calibration control terminal 410 and/or the human operator may adjust one or more of the operating parameters 129 as generally shown in FIGS. 19-22. FIGS. 19 and 20 provide a first example, and FIGS. 21 and 22 provide a second example. FIG. 19 is a plot of artifact visibility (ordinate 472) against one or more of the operating parameters 129 (abscissa 474). Two curves 476 and 478 respectively represent the visibility of artifacts at two different gray levels. In the example of FIG. 19, the gray levels selected are gray level G63 (curve 476) and gray level G127 (curve 478). Here, the gray level G63 may be chosen because the mura artifacts have the possibility to be strongest in a positive sense at gray level G63. The gray level G127 may be chosen because the mura artifacts have the possibility to be strongest in a negative sense at G127. In other embodiments, however, any other suitable gray levels may be selected. As illustrated in plot 470, as the parameter(s) 129 are dialed up or down, the extent to which the mura artifacts become more or less visible may depend on the gray level being displayed on the display 18. Where both curves 476 and 478 fall within a specified range 480, the display 18 may be understood to be well calibrated. Points A, B, C, D, and E of the plot 470 refer to points associated with a flowchart 490 shown in FIG. 20.

The flowchart 490 of FIG. 20 may begin when the pixels of the display 18 are set to display a gray level of G63 (block 492). When this occurs, the display 18 may be understood to be displaying mura artifacts at a level associated with point A on the plot 470 of FIG. 19. The calibration control terminal 410 and/or a human operator may dial the parameter(s) 129 down until the artifact(s) are substantially eliminated (block 494). This may entail changing the parameter(s) 129 in discrete amounts until the artifacts begin to appear inverted, as may occur at point B of FIG. 19. The parameter(s) 129 may be walked back one discrete step to be approximately to what likely may be the lowest visibility of the artifacts when the display 18 is displaying a gray level of G63, corresponding to point C of FIG. 19.

Although, the display 18 may show few or no mura artifacts at the gray level G63, it is possible that the mura artifacts may be excessive at another gray level (e.g., G127). Thus, the calibration control terminal 410 and/or the human operator next may set the gray level to G127 (block 496). In this example, the level of artifacts seen when the gray level is changed may be visualized as point D of the plot 470 of FIG. 19. The calibration control terminal 410 and/or the human operator then may observe whether the luminance contrast of the mura artifacts are within the specified bounds (e.g., within the specified range 480) (block 498).

In the example of FIG. 19, point D occurs within the specified range 480. Thus, the calibration control terminal 410 or the human operator may observe that the mura artifact visibility is within the specification (decision block 500). The calibration control terminal 410 thus may store the parameter(s) 129 in the display 18 (block 502). It is possible, depending on the specified range 480 and the distribution of the curves 476 and 478, that the artifact visibility at point D could fall outside of the specified range 480 (decision block 500). When this is the case (decision block 500), the parameter(s) 129 may be walked back in discrete amounts (block 504) until the value is within the specified range 480. In some embodiments, the discrete steps of changes in the parameter(s) 129 may be larger when initially determining the point along the gray level G63 curve 476 where no artifacts occur (e.g., point C). The discrete steps of changes in the parameter(s) 129 may be smaller when moving along the gray level G126 curve 478 (e.g., half the size of the discrete steps at the gray level G63).

In another example, illustrated in FIGS. 21 and 22, ideal artifact correction on both curves 476 and 478 may be initially determined, and an intermediate value may be selected based on these two values. A plot 508 of FIG. 21 is substantially the same as the plot 470 of FIG. 19, except that different points are shown. The points A, B, C, D, E, and F of the plot 508 correspond to blocks of a flowchart 510 of FIG. 22. The flowchart 510 of FIG. 22 may begin when the calibration control terminal 410 sets the gray level of the display2G63 (block 512). This may correspond to point A on the plot 508 of FIG. 21. The calibration control terminal 410 may gradually adjust the parameter(s) 129 in discrete steps until the mura artifacts are inverted at point B, then stepping back one discrete step such that the mura artifacts are substantially at zero at point C (block 514). The value of the parameter(s) 129 reached at block 514 at point C may be temporarily stored in the memory 418 of the calibration control terminal 410. This value may be used in determining the ultimate intermediate parameter(s) 129 that may be stored in the display 18.

Next, the calibration control terminal 410 may determine values of the operating parameter(s) 129 that similarly causes the display 18 to reach a zero-point for the gray level G127. Thus, the calibration control terminal 410 may cause the display 18 to display a gray level of G127 (block 516). This may correspond to point D in the plot 508 of FIG. 21. Thus, an inverted artifact may be visible on the display 18 at block 516. The calibration control terminal 410 may adjust the parameter(s) 129 by stepping back in discrete steps until reaching a zero-point at the gray level of G127 (block 518). In the plot 508 of FIG. 21, this may correspond to stepping until the artifact seen at the gray level G127 become inverted from the original point D to point E along the curve 478. The calibration control terminal 410 then may walk back the parameter(s) 129 by one step to achieve a very low level of mura artifacts (e.g., substantially zero artifacts) at point F. The memory 418 of the calibration control terminal 410 may store this value of the parameter(s) 129.

At block 520 of FIG. 22, the values of the parameter(s) 129 obtained at block 514 and 518 may be used to determine an intermediate value of the operating parameter(s) 129. This intermediate value of the operating parameter(s) 129 may cause both the gray level G63 and gray level G127 to fall within the specified range 480 (block 520), though neither may necessarily be completely artifact-free. To do so, the calibration control terminal 410 may select an absolute average, a weighted average, or may use the values from blocks 514 and 518 in any other suitable function to determine an intermediate parameter(s) 129 value. The calibration control terminal 410 then may store the determined intermediate parameter(s) 129 value in the display 18 (block 522).

Figure 23:
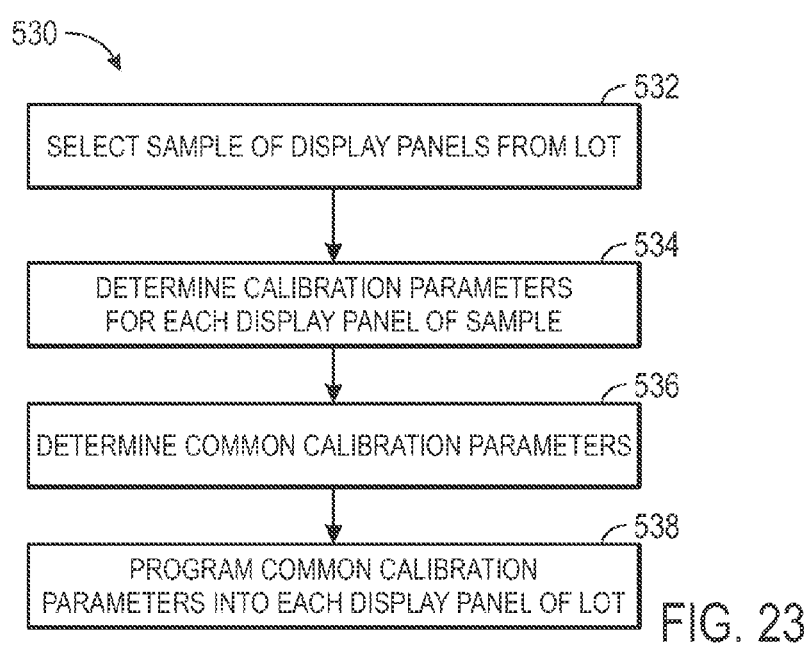
FIG. 23 is a flowchart of a method for calibrating a lot of LCDs, in accordance with an embodiment.

Regardless of the calibration approach used, displays 18 may be calibrated individually or by lot. For example, as shown by a flowchart 530 of FIG. 23, only some samples of displays 18 may be selected from a lot or batch being manufactured (block 532). Suitable calibration parameter(s) 129 thus may be determined for each display 18 in the sample (block 534). Using any suitable statistical method, common calibration parameter(s) may be determined for the sample (block 536). For example, a median or model value of calibration parameter(s) 129 that causes the display 18 of the sample to all fall within a specified range of suitable artifacts visibility may be determined. The common calibration parameter(s) associated with the statistical sample may be programmed into each display 18 of the lot (block 538).

The severity of the mura artifact(s) may relate to a temperature of the display 18. For instance, it is believed that vertical stripe feature of merit (VSFOM) artifacts may become more pronounced at higher temperatures. Thus, the common calibration parameter(s) 129 that are selected may be selected such that the displays 18 of the lot of displays may remain within a specified range despite variations in temperature. To account for these temperature variations, the sample of the display panels obtained from the lot of displays 18 may include a suitable range of operating temperatures. The distribution of temperatures in the sample may be selected experimentally, as may be the sample size, such that the resulting common calibration parameter(s) 129 may keep the display panels 18 within the specified range 480 despite changes in temperature.

Figure 24:
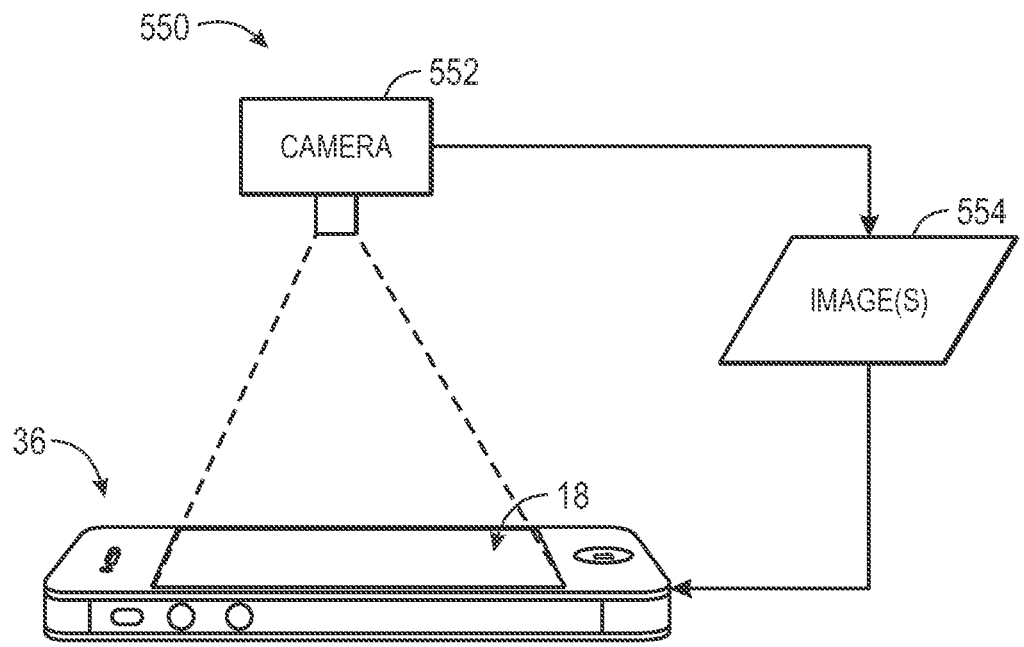
FIG. 24 is a block diagram of a system for calibrating the LCD after the LCD has been installed in an electronic device, in accordance with an embodiment.
Figure 25:
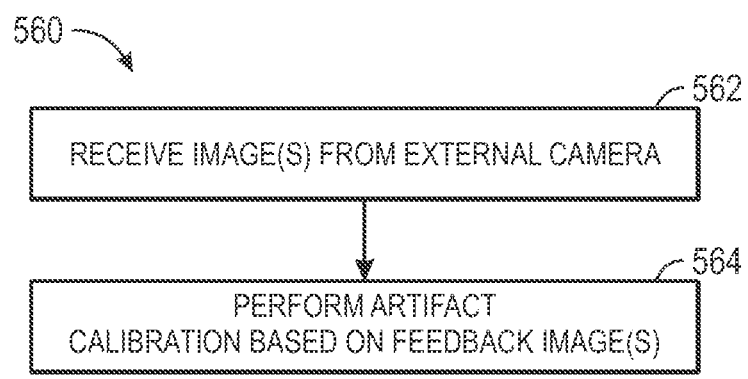
FIG. 25 is a flowchart for calibrating the LCD using the system of FIG. 24, in accordance with an embodiment.

The various techniques and systems discussed above also may apply after the display 18 has been installed within an electronic device 10. For instance, the calibration control terminal 410 and/or the human operator may adjust the parameter(s) 129 of the display 18 through the electronic device 10 where the display 18 may already be installed. Additionally or alternatively, the processor(s) 12 of the electronic device 10 may operate as the calibration control terminal 410, as illustrated in FIG. 24. In a calibration system 550 of FIG. 24, a camera 552 may supply images 554 of the display 18 of an electronic device 10, here shown as the handheld device 36. The handheld device 36 may vary the operation of the display 18 according to any suitable calibration technique, including those discussed above. Thus, as illustrated by a flowchart 560 of FIG. 25, the electronic device 10 may receive images from an external camera such as the camera 552 (block 562). The electronic device 10, such as the handheld device 36 shown in FIG. 24, may perform any suitable calibration techniques using the feedback images 554 (block 564).

Figure 26:
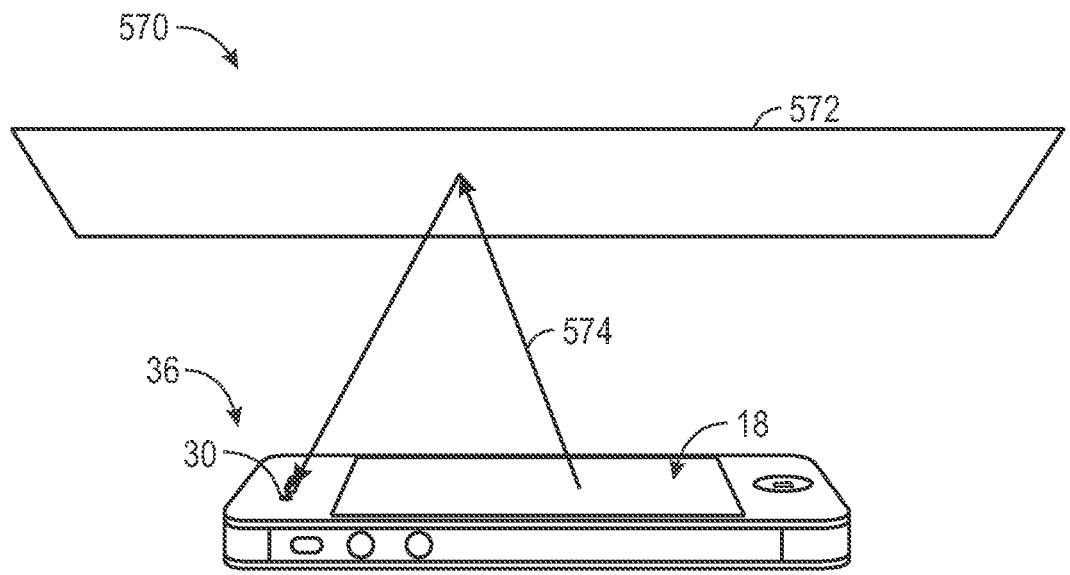
FIG. 26 is a block diagram of another system for calibrating the LCD after the LCD has been installed in the electronic device using an onboard camera, in accordance with an embodiment.

In some embodiments, an electronic device 10, such as the handheld device 36, may avoid using an external camera, relying instead on its onboard camera 30, as illustrated in FIG. 26. In FIG. 26, a calibration system 570 includes an electronic device 10, here shown as the handheld device 36 and a reflective surface 572. The reflective surface 572 may be any suitable surface that can reflect light 574 with suitable clarity such that mura artifacts on the display 18 are perceptible by the camera 30 of the electronic device 10. In addition, in some embodiments, the camera 30 may be of a sufficiently high dynamic range so as to be able to distinguish the artifacts without amplification. For instance, the camera 30 may capture a dynamic range of 12 bits or higher when the mura artifacts may be up to one-fifth of a gray level.

Figure 27:
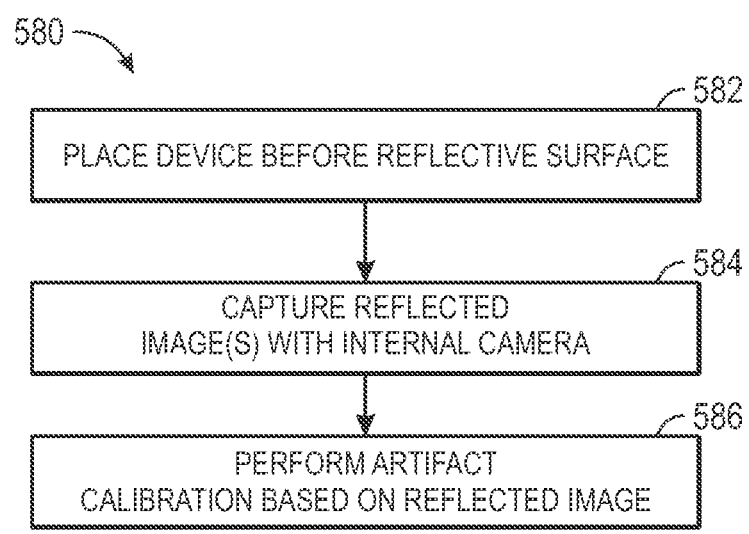
FIG. 27 is a flowchart of a method for calibrating the LCD using the system of FIG. 26, in accordance with an embodiment.

The system 570 of FIG. 26 may operate in a manner described by a flowchart 580 of FIG. 27. The flowchart 580 may begin when the electronic device 10 is placed before the reflective surface 572 (block 582). In certain embodiments, more than one reflective surface 572 may be employed, and the light 574 may be redirected to a back-facing camera 30 rather than a front-facing camera 30 as shown in FIG. 26. The flowchart 580 of FIG. 27 may continue when the onboard camera 30 of the electronic device 10 captures reflective images of the display 18 (block 584). Using these images as feedback, the electronic device 10 may perform any suitable artifact calibration techniques, including those discussed above (block 586).

Figure 28:
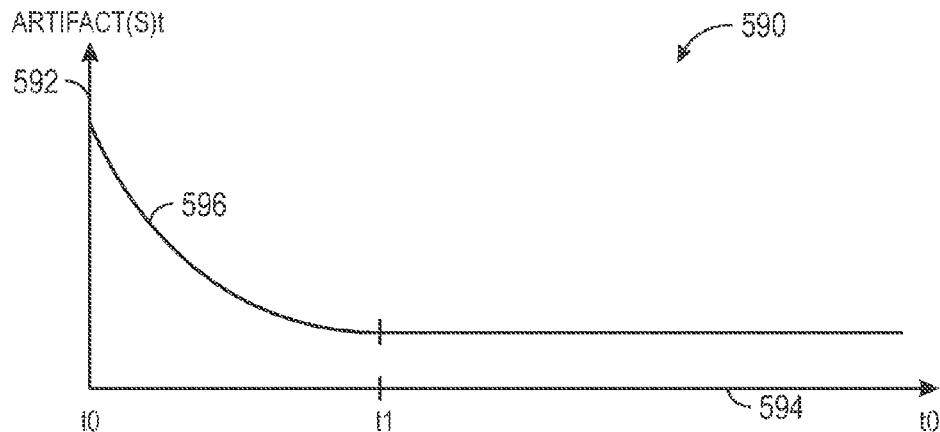
FIG. 28 is a luminance plot of certain mura artifacts over time, in accordance with an embodiment.
Figure 29:
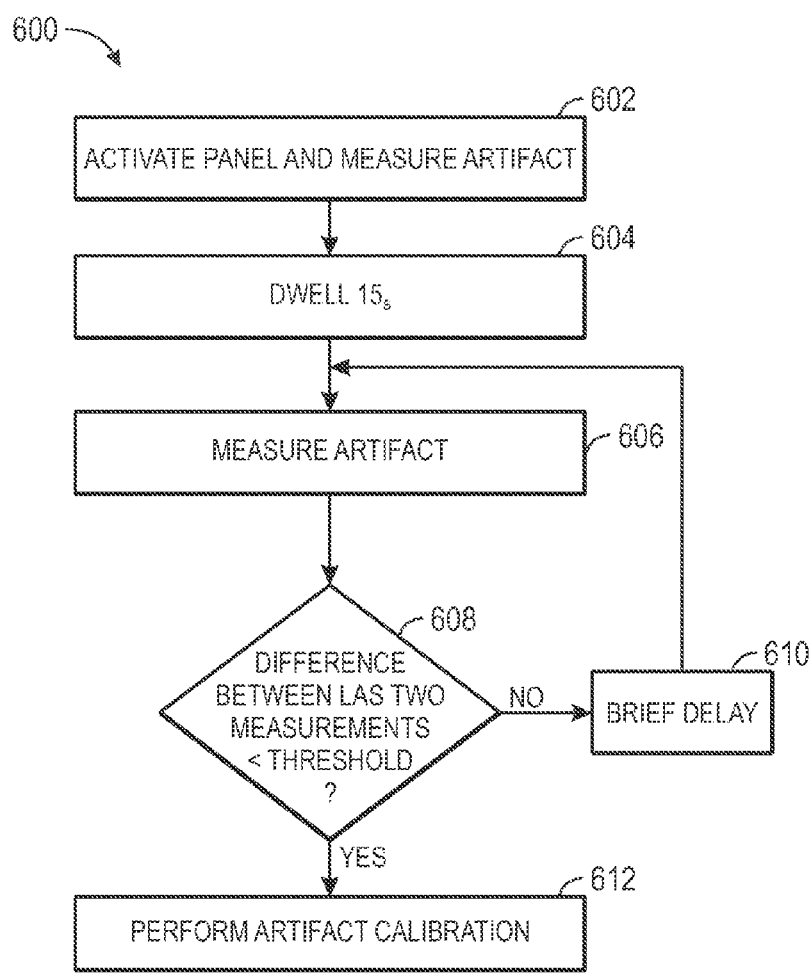
FIG. 29 is a flowchart of a method for choosing when to begin calibrating the LCD to account for the transient behavior of certain mura artifacts, in accordance with an embodiment.

The mura artifact discussed above may have a transient character. For instance, as shown by a plot 590 of FIG. 28, the visibility of the artifacts (ordinate 592) may vary with time (abscissa 594). A curve 596 of artifact visibility thus may decrease substantially exponentially between an initial time $t_0$ and a settling time $t_1$. Calibrating the display 18 before the display 18 has reached the settling time $t_1$ could produce inaccurate parameter(s) 129 that do not fully reduce or eliminate the artifact(s). As such, before calibrating the display 18, the display 18 may be allowed to dwell for some period of time, as generally represented by a flowchart 600 of FIG. 29.

Since the settling time $t_1$ may vary from display 18 to display 18, the flowchart 600 may aim to begin calibrating the display 18 as soon as the mura artifact is settled. The flowchart 600 may begin when the display 18 is initially activated and the luminance of the artifact may be measured (block 602). For instance, the camera 406, 552, or 30 may determine a luminance difference between the bright areas and dark areas of the artifact(s) or simply a luminance of one of either the bright or the dark areas. The display 18 then may be allowed to dwell—that is, to remain on—for some period of time (block 604). In the example of the flowchart 600, this amount of time is 15 seconds. Any suitable amount of time may be chosen, however, depending on the characteristics of the display panels 18. Having given the display 18 an opportunity to dissipate some of the artifact(s), the luminance difference of the artifact(s) may be measured again (block 606).

Since the settling time $t_l$ may vary from display 18 to display 18, the display 18 may be deemed to have settled once the difference between the latest two measurements has changed less than a given magnitude. Thus, if the magnitude of the difference between the latest two measurements exceeds some threshold (e.g., around 300 $cd/m^2$), it may understood that the artifact has not yet settled, (block 608), and so the display 18 may be allowed to dwell an additional period of time (block 610). The threshold may be selected depending on the characteristics of the display panels 18 being manufactured. In some cases, the threshold may be selected by batch or lot, and/or may be adjusted as more displays from the batch or lot are calibrated. For instance, in some embodiments, the threshold may be relatively small (e.g., 100 candela per meter squared ($cd/m^2$) or less), while in other embodiments, the threshold may be coarser (e.g., 500 $cd/m^2$ or even greater). The additional period of time may be any suitable period of time, lasting from less than one second to a few seconds. In some embodiments, the delay period of block 610 may be the same as the first period of delay (e.g., 15 seconds).

On the other hand, if the magnitude of the difference between the latest two luminance measurements does exceed the threshold (decision block 608), the display 18 may be understood to have reached sufficiently near to its settling value (e.g., at $t_1$ and beyond). Artifact calibration may than may be performed (block 612) without concern that the severity of the artifact(s) will change dramatically during the course of calibration.

Another concern that may be addressed before calibrating the display 18 for mura artifacts may be flicker induced by bias voltages accumulating in the display 18. Such bias voltages may arise due to differences between an ideal common voltage (VCOM) value supplied to the common electrodes 112 and the actual VCOM value supplied to the common electrodes 112. In another example, these bias voltages may appear due to stray charges introduced into the display 18 during the manufacture of the display 18 or the electronic device 10 in which the display 18 has been installed. Both of these potential sources of display 18 flicker will be addressed below.

Figure 30:
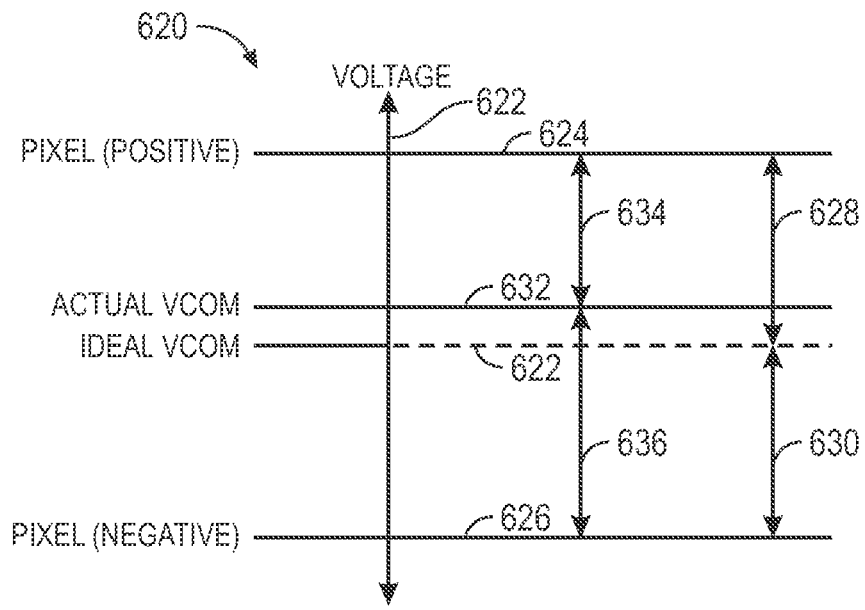
FIG. 30 is a voltage diagram comparing positive and negative pixel voltages to an ideal and an actual VCOM voltage, in accordance with an embodiment.

Turning to FIG. 30, a voltage diagram 620 illustrates one reason bias voltages may build up in the display 18 as the display 18 operates. It may be recalled that the display 18 pixels 102 operate by varying an electric field through the liquid crystal material of each pixel. To generate the electric field, the common electrode 112 may be maintained at a generally uniform DC level over time. The voltage value supplied on the pixel electrodes 110, however, may be some voltage value higher or lower than the VCOM voltage supplied to the common electrode 110 to produce the electric field. Since maintaining the same polarity on the pixel electrodes 110 for an extended period of time could be problematic, the polarity of the voltage supplied to the pixel electrodes 110 may vary occasionally (e.g., on a frame-by-frame basis).

These values are generally reflected in the voltage diagram 620 of FIG. 30. Several voltages of these display 18 components are located along a voltage axis 622. Namely, an ideal value of a VCOM voltage is shown at line 622, a positive polarity of a voltage supplied to a pixel electrode 110 appears at line 624, and a negative polarity of a voltage value supplied to a pixel electrode 110 is shown at line 626. The voltages at line 624 and 626 have been selected such that magnitude 628 and 630 are the same. This ensures that the electric fields produced by the positive pixel values of 624 and negative pixel values 626 have substantially the same effect on the liquid crystal material of each pixel 102 of the display 18.

In reality, however, the actual VCOM value may differ from the ideal VCOM value. In the voltage diagram 620 of FIG. 30, an actual VCOM value is provided as an example at line 632, which differs somewhat from the ideal VCOM value at 622. The magnitude of the value between the actual VCOM voltage and the positive and negative polarities appears as magnitudes 634 and 636. Since the magnitudes 634 and 636 are not the same, the electric field produced by these values is slightly different and flicker may result. Specifically, when the pixels 102 of the display 18 are supplied with alternating polarities of data signals, and the magnitudes 634 and 636 result, the pixels 102 generally may spend more time at a slightly more negative polarity than at the positive polarity. As such, bias voltages (e.g., in the negative direction, in the voltage diagram 620 of FIG. 30), may form in the display 18. This produces flicker, which may make the mura artifacts more difficult to correct in the calibration techniques discussed above. As such, the displays 18 may be tuned to correct flicker before addressing the mura artifacts.

Figure 31:
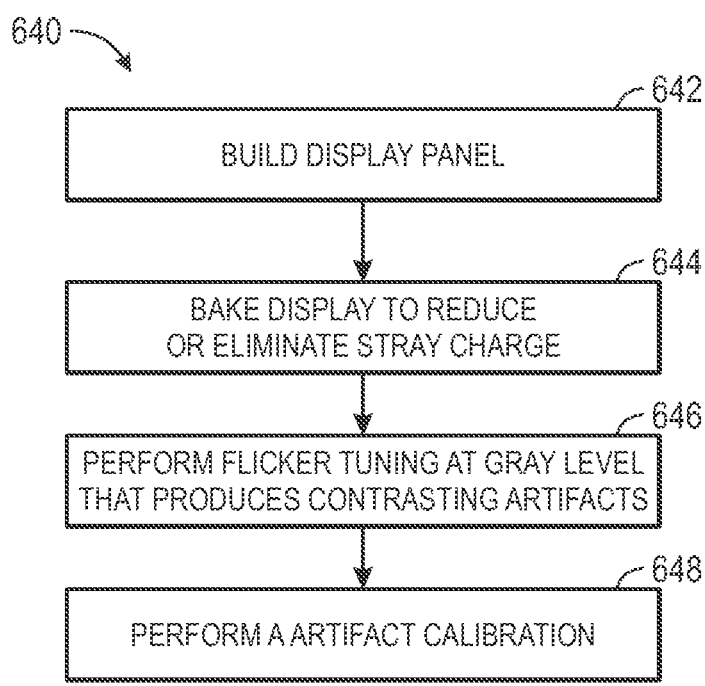
FIG. 31 is a flowchart of a method for reducing stray charge or other artifacts before calibrating the LCD for certain mura artifacts, in accordance with an embodiment.

Even before eliminating flicker artifacts, reducing or eliminating stray charges due to various steps in the manufacturing process of the display 18 and/or the electronic device 10 into which the display 18 has been installed may be warranted. For example, as shown by a flowchart 640 of FIG. 31, once a display panel has been largely built (block 642), the display 18 may be baked to cause stray charge to the reduced or eliminated (block 644). In particular, the display 18 and/or the electronic device 10 (if the display 18 has already been installed) may be baked at a relatively high temperature (e.g., around 50° C.) for a period of time suitable to reduce or eliminate the stray charges on the display 18. In certain embodiments, the display 18 may be baked in relatively high humidity (e.g., around approximately 50% humidity) to reduce the chance of electrostatic discharge (ESD) events. The temperature selected may be any suitably high temperature that causes stray charge to more easily dissipate from the display 18, while remaining low enough not to damage components of the display 18. Similarly, the humidity may be selected to be high enough to prevent ESD events on the display 18, while remaining low enough not to cause short-circuiting of the display 18.

After baking the display 18, flicker tuning may be performed (block 646). Flicker tuning may be carried out using any suitable technique, such as adjusting the VCOM voltage values while observing the amount with the degree to which the display 18 exhibits flickering. In some embodiments, the flicker tuning may take place while the display 18 is displaying a gray level that suitably produces contrasting artifacts on the display mura artifacts on the display 18. For instance, the gray level may be selected to be the primary gray level used in mura artifact calibration. Thus, the gray level may be selected to be a gray level that produces the greatest contrast in the mura artifacts. In one embodiment, this gray level may be a gray level of G63. By tuning for flicker at the gray level that produces contrasting mura artifacts on the display 18, artifact calibration (block 648) may be performed on a display 18 with reduced flicker and/or negative effects due to stray charge on the display 18. Any suitable mura artifact calibration may be performed, including any of those discussed above.

Technical effects of the present disclosure include the manufacture of a display having multiple common voltage layers (VCOMs) with improved image quality. Namely, despite the presence of multiple VCOMs in the display, mura artifacts, such as vertical striping artifacts, may be reduced or eliminated. These techniques may be performed with assistance from a human operator or automatically by a control terminal. By dynamically accounting for the transient character of certain mura artifacts, calibrating the mura artifacts may be carried out both precisely and efficiently. Moreover, by baking the display to reduce or eliminate stray charge before performing flicker tuning, the resulting displays may exhibit fewer flickering artifacts or defects due to stray charge.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A method comprising:
turning on an electronic display;
programming pixels the electronic display to a uniform gray level;
measuring an initial luminance of the pixels;
waiting a first period of time;
measuring a subsequent luminance of the pixels;
calibrating the display to reduce artifacts when a magnitude of a difference between the subsequent luminance and the initial luminance is within a threshold; and
when the magnitude of the difference between the subsequent luminance and the initial luminance does not exceed the threshold:
waiting a second period of time; and
remeasuring the subsequent luminance of the pixels;
wherein the display is calibrated to reduce artifacts when a magnitude of a difference between the latest two measurements of luminance is within the threshold.

2. The method of claim 1, wherein measuring the initial luminance and measuring the subsequent luminance comprise measuring an absolute value of luminance of a subset of the pixels that are brighter or darker than another subset of the pixels.

3. The method of claim 1, wherein measuring the initial luminance and measuring the subsequent luminance comprise measuring a difference between a first subset of the pixels and a second subset of the pixels, wherein the first subset of the pixels is brighter or darker than the second subset of the pixels.

4. The method of claim 1, wherein the first period of time is longer than the second period of time.

5. The method of claim 1, wherein the gray level is configured to produce a stronger contrast of a mura artifact than most other gray levels.

6. The method of claim 1, wherein the gray level is a gray level between G40 to G80 on a scale from G0 to G255.

7. The method of claim 1, wherein the gray level is configured to produce a stronger contrast of a mura artifact than all other gray levels.

8. The method of claim 1, wherein the gray level is a gray level of G63 on a scale from G0 to G255.

9. A system for calibrating an electronic display, comprising:
a camera configured to capture images of an active area of an electronic display while the electronic display is programmed to a uniform gray level, such that a mura artifact of the electronic display is enhanced relative to most other gray levels; and
a computer configured to:
receive a first image of the electronic display when the electronic display is turned on and programmed to the uniform gray level;
determine a first luminance difference between bright areas and dark areas of the mura artifact in the first image;
wait a first period of time;
receive a second image of the electronic display;
determine a second luminance difference between the bright areas and dark areas of the mura artifact in the second image; when the magnitude of the difference between the second luminance and the first luminance does not exceed a threshold:
wait a second period of time;
receive a third image of the electronic display;

determine a third luminance difference between the bright areas and dark areas of the mura artifact in the third image; and indicate that the display is ready to be calibrated to reduce or eliminate the mura artifact when a magnitude of a difference between the third luminance and the second luminance is within the threshold.

10. The system of claim 9, wherein the threshold is configured to indicate that the mura artifact has stabilized.

11. The system of claim 9, wherein the threshold is less than or equal to about 300 cd/m$^2$.

12. The system of claim 9, wherein the threshold is less than or equal to about 100 cd/m$^2$.

13. The system of claim 9, wherein the threshold is greater than about 500 cd/m$^2$.

14. The system of claim 9, wherein the camera is configured to obtain images of a bit depth sufficient to detect the mura artifact.

15. The system of claim 9, wherein the camera is configured to obtain images having a bit depth of 12 or greater.

16. A method of manufacturing an electronic device, comprising:

installing an electronic display into the electronic device;

turning on the electronic device;

programming pixels of the electronic display to a first gray level;

determining luminance values output by the pixels at a first point in time and a second point in time;

when the magnitude of the difference between the luminance value at the first time and the luminance value at the second time does not exceed a threshold:

waiting until a third point in time; and determining a luminance value output by the pixels at the third point in time; and starting to calibrate the electronic display to reduce a mura artifact when the luminance value at the second point in time and the luminance value at the third point in time are different from one another by less than the threshold value.

17. The method of claim 16, wherein the electronic display comprises a liquid crystal display comprising a plurality of common voltage layers (VCOMs) and wherein the mura artifact is due at least in part to differential characteristics of the VCOMs.

18. The method of claim 16, wherein the electronic device comprises a handheld device, a portable phone, a notebook computer, a tablet computer, or a desktop computer, or any combination thereof.

19. An electronic device comprising:
an electronic display; and
a processor configured to:
cause pixels of the electronic display to be programmed to a gray level;
periodically receive substantially real-time images of the pixels of electronic display;
determine luminance values of the pixels of a first image and a second image; and
calibrate the electronic display after luminance values from the first image and a second image are different by less than a threshold;
when the luminance values from the first image and the second image are different by more than the threshold:
wait for a third received image;
determine luminance values of the pixels of a third image; and
calibrate the electronic display after luminance values from the second image and the third image are different by less than the threshold.

20. The electronic device of claim 19, comprising a camera configured to capture the images of the pixels of the electronic display via a reflective material directing light from the electronic display to the camera.

21. The electronic device of claim 19, wherein the processor is configured to receive the images from an external source, wherein the images derive from a camera external to the electronic device.

22. One or more articles of manufacture comprising:
one or more tangible, machine-readable media comprising processor-executable instructions to:
periodically receive real-time images of an electronic display programmed to display a single gray level;
when luminance differences between light and dark areas of the electronic display apparent in a first real-time image and a second real time image of the electronic display are different from one another by greater than a threshold value, wait until receiving a third real-time image; and
when luminance differences between light and dark areas of the electronic display apparent in the second real-time image and the third real-time image of the electronic display are different from one another by less than a threshold value:
indicate that a mura of the electronic display has stabilized; or
start to tune the electronic display to reduce or eliminate the mura; or
both.

* * * * *